(12) United States Patent
Miller et al.

(10) Patent No.: US 12,070,222 B2
(45) Date of Patent: Aug. 27, 2024

(54) APPARATUS AND METHOD FOR TEMPORARY OCCLUSION OF BLOOD VESSELS

(71) Applicant: Amsel Medical Corporation, Cambridge, MA (US)

(72) Inventors: Arnold Miller, Cambridge, MA (US); Raanan Miller, Cambridge, MA (US); Nir Lilach, Kfar Yehoshua (IL); William E. Edelman, Sharon, MA (US)

(73) Assignee: Amsel Medical Corporation, Cambridge, MA (US)

( * ) Notice: Subject to any disclaimer, the term of this patent is extended or adjusted under 35 U.S.C. 154(b) by 748 days.

(21) Appl. No.: 16/435,436

(22) Filed: Jun. 7, 2019

(65) Prior Publication Data

US 2021/0007746 A1    Jan. 14, 2021

Related U.S. Application Data

(63) Continuation-in-part of application No. 15/044,323, filed on Feb. 16, 2016, now Pat. No. 10,631,870, (Continued)

(51) Int. Cl.
*A61B 17/122* (2006.01)
*A61B 17/064* (2006.01)
(Continued)

(52) U.S. Cl.
CPC .......... *A61B 17/122* (2013.01); *A61B 17/12* (2013.01); *A61B 17/12009* (2013.01);
(Continued)

(58) Field of Classification Search
CPC . A61B 17/12; A61B 17/122; A61B 17/12013; A61B 17/1227; A61B 17/128; A61B 17/1285; A61B 2017/12004; A61B 17/00008; A61B 17/12009; A61B 17/12022; A61B 17/1214;
(Continued)

(56) References Cited

U.S. PATENT DOCUMENTS

| 5,865,791 A | 2/1999 | Whayne |
| 6,071,292 A | 6/2000 | Makower |

(Continued)

FOREIGN PATENT DOCUMENTS

| WO | WO2005053547 | 6/2005 |
| WO | WO2018090061 | 5/2018 |

OTHER PUBLICATIONS

U.S. Appl. No. 65/551,333, issue date Feb. 22, 2003, Kuhne.

*Primary Examiner* — Sarah W Aleman
*Assistant Examiner* — Mikail A Mannan
(74) *Attorney, Agent, or Firm* — Bookstein IP Law

(57) ABSTRACT

Methods and devices for temporarily occluding blood vessels are provided for use in emergency conditions to control trauma-induced hemorrhaging. An occlusion device is delivered and deployed through a rapidly introduced, percutaneously placed needle that carries an occlusion device in readiness to be deployed out of the needle. The deployed occlusion device applies pressure to the target blood vessel to control blood loss.

20 Claims, 29 Drawing Sheets

Related U.S. Application Data which is a continuation of application No. 13/857,424, filed on Apr. 5, 2013, now abandoned, and a continuation-in-part of application No. 13/348,416, filed on Jan. 11, 2012, now abandoned.

(60) Provisional application No. 62/687,467, filed on Jun. 20, 2018, provisional application No. 62/682,719, filed on Jun. 8, 2018, provisional application No. 61/620,787, filed on Apr. 5, 2012, provisional application No. 61/431,609, filed on Jan. 11, 2011.

(51) Int. Cl.
*A61B 17/12* (2006.01)
*A61B 17/128* (2006.01)
*A61B 17/00* (2006.01)

(52) U.S. Cl.
CPC .... *A61B 17/12022* (2013.01); *A61B 17/1214* (2013.01); *A61B 17/12145* (2013.01); *A61B 17/1285* (2013.01); *A61B 2017/00867* (2013.01); *A61B 2017/00986* (2013.01); *A61B 17/0643* (2013.01); *A61B 2017/12054* (2013.01)

(58) Field of Classification Search
CPC .......... A61B 17/12145; A61B 17/0643; A61B 2017/00867; A61B 2017/00986; A61B 2017/12054; A61B 17/0467; A61B 2017/0417; A61B 2017/0464; A61B 2017/0496

See application file for complete search history.

(56) References Cited

U.S. PATENT DOCUMENTS

| | | |
|---|---|---|
| 6,293,995 B2 | 9/2001 | Houser |
| 6,312,446 B1 | 11/2001 | Huebsch |
| 7,361,180 B2 * | 4/2008 | Saadat .................. A61B 17/08 |
| | | 606/205 |
| 7,491,232 B2 | 2/2009 | Bolduc |
| 7,798,953 B1 | 9/2010 | Wilk |
| 8,133,242 B1 * | 3/2012 | Quinn .................. A61B 17/122 |
| | | 606/142 |
| 8,257,389 B2 | 9/2012 | Chanduszko |
| 10,548,610 B2 | 2/2020 | Bradley |
| 2005/0267524 A1 | 12/2005 | Chanduszko |
| 2005/0267529 A1 | 12/2005 | Crockett |
| 2005/0288786 A1 | 12/2005 | Chanduszko |
| 2007/0049970 A1 | 3/2007 | Belef |
| 2007/0106328 A1 | 5/2007 | Wardla |
| 2007/0248640 A1 | 10/2007 | Karabey |
| 2007/0265658 A1 | 11/2007 | Nelson |
| 2008/0208226 A1 | 8/2008 | Siebold |
| 2009/0084386 A1 | 4/2009 | McClellan |
| 2011/0082495 A1 | 4/2011 | Ruiz |
| 2011/0108039 A1 | 5/2011 | Frigstad |
| 2011/0160538 A1 * | 6/2011 | Ravikumar ........ A61B 17/0218 |
| | | 606/192 |
| 2013/0010154 A1 | 1/2013 | Maeda |
| 2013/0046331 A1 | 2/2013 | Christensen |
| 2014/0243857 A1 | 8/2014 | Miller et al. |
| 2015/0066139 A1 | 5/2015 | Van Bladel |
| 2015/0202381 A1 | 7/2015 | Schatz |
| 2015/0290428 A1 | 10/2015 | Tkebuchava |
| 2018/0214270 A1 | 8/2018 | Subramanian |
| 2019/0290419 A1 | 9/2019 | Willard |

* cited by examiner

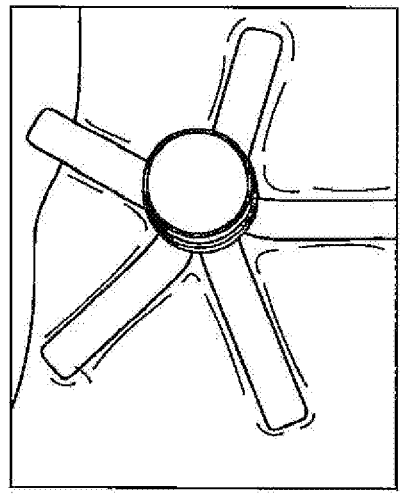
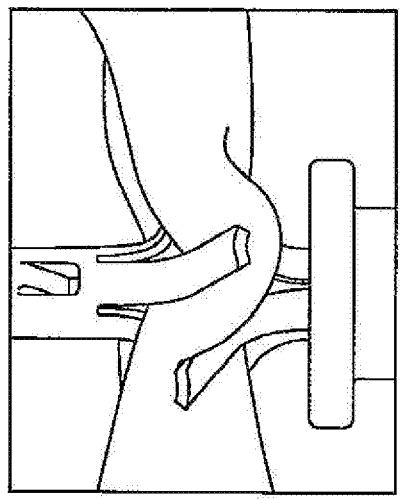
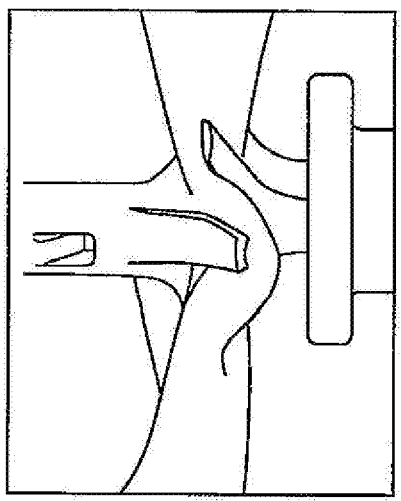
FIG. 16

The occlusion is adjustable
Slide the knob and lock it in the desired position.

1st step - Penetration of the vessel with the needle.
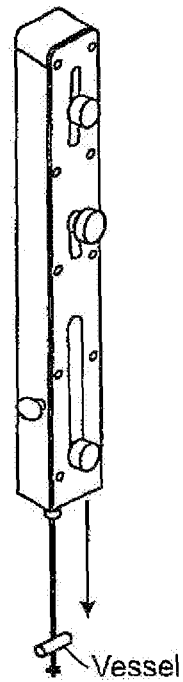
Vessel
FIG. 19
2nd step - Reveal the distal clip by sliding the distal slider forward.
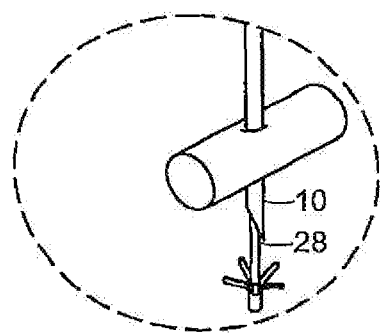
FIG. 20

3rd step - Pull the device in order to tighten the distal clip towards the vessel wall.
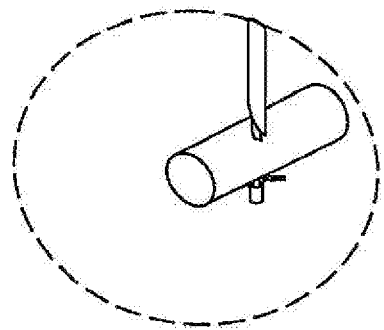
FIG. 21
4th step - Slide the needle slider backward in order to reveal the proximal clip.
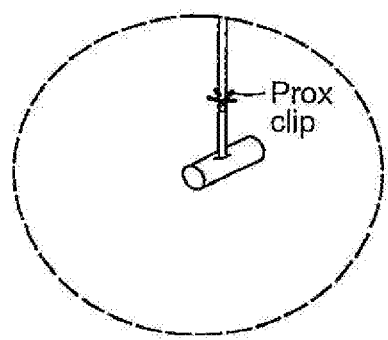
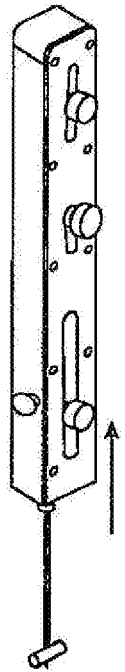
FIG. 22

5th step (optional) - Slide the proximal slider half way forward in order to occlude partially the vessel.
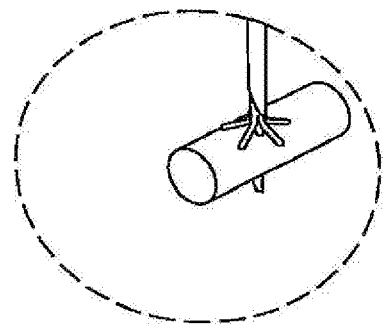 
FIG. 23
6th step - Slide the proximal slider all the way forward in order to occlude completely the vessel.
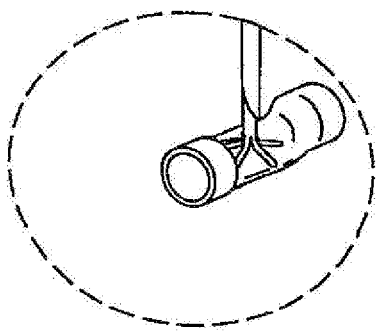 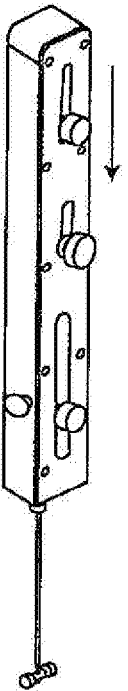
FIG. 24

7th step – Removing the safety pin make it possible to slide the needle all the way backward and enable to 'fold' the device.

8th step – 'Folding' the device while it is connected to the patient body.

APPARATUS AND METHOD FOR TEMPORARY OCCLUSION OF BLOOD VESSELS

RELATED APPLICATIONS

This patent application:
(i) is a continuation-in-part of pending prior U.S. patent application Ser. No. 15/044,323, filed Feb. 16, 2016 by Arnold Miller, et al. for METHOD AND APPARATUS FOR OCCLUDING A BLOOD VESSEL which
  (a) is a continuation of abandoned U.S. patent application Ser. No. 13/857,424, filed Apr. 5, 2013 by Arnold Miller et al for Method and Apparatus for Occluding a Blood Vessel which claimed benefit of U.S. provisional patent application 61/620,787 filed Apr. 5, 2012 and
  (b) is a continuation-in-part of prior U.S. patent application Ser. No. 13/348,416, filed Jan. 11, 2012 by Arnold Miller et al. for METHOD AND APPARATUS FOR TREATING VARICOSE VEINS (abandoned), which patent application claimed benefit of prior U.S. provisional patent application Ser. No. 61/431,609, filed Jan. 11, 2011 by Arnold Miller for METHOD AND APPARATUS FOR TREATING VARICOSE VEINS;
  and claimed benefit of prior U.S. provisional patent application Ser. No. 61/620,787, filed Apr. 5, 2012 by Arnold Miller et al. for TEMPORARY ARTERIAL OCCLUSION FOR MILITARY AND CIVILIAN EXTREMITY TRAUMA;
(ii) This application also claims benefit of pending U.S. provisional patent application Ser. No. 62/682,719, filed Jun. 8, 2019 by Arnold Miller, et al. for METHOD AND APPARATUS FOR TEMPORARY OCCLUSION OF BLOOD VESSELS; and
(iii) claims benefit of pending U.S. provisional patent application Ser. No. 62/687,467, filed Jun. 20, 2018 by Arnold Miller, et al. for METHOD AND APPARATUS FOR TEMPORARY OCCLUSION OF BLOOD VESSELS.

The disclosures of the seven (7) above-identified patent applications are hereby incorporated herein by reference in their entireties.

FIELD

This application relates to methods and devices for temporarily occluding blood vessels, including blood vessels in organs for example, in situations where one has received an injury and is experiencing significant blood loss.

BACKGROUND

Uncontrolled hemorrhage remains the most significant cause of death in victims who survive a major initial trauma, particularly in truncal and extremity injuries. A loss of 50% of blood volume without replenishment is frequently fatal, and a hypotensive patient, who has lost 30%-35% of blood volume and is in uncompensated shock, is generally close to death. Establishing and maintaining hemo stasis at or around the site of an injury is an important consideration in the acute management of trauma patients. The tourniquet, with or without local compression, remains the time-honored method for controlling extremity bleeding following trauma. However, tourniquets generally are useful only for controlling bleeding in limbs, and even then, tourniquets suffer from the disadvantage that they limit blood flow to the entire limb and cannot target individual blood vessels within the limb. It is estimated that of all military wounded who ultimately succumb to their wounds, approximately 10-20% die from blood loss due to inadequate compression or tourniquet application. There is a need for more effective temporary blood vessel occlusion techniques and devices for military as well as civilian trauma cases.

In addition to trauma applications, there may be various medical procedures in which an occlusion device may be implanted and then, at a later time (e.g., days, weeks, months), may be removed, for example in reversible occlusion of fallopian tubes or temporary occlusion of the saphenous vein during pregnancy with subsequent removal of the occlusion device at the conclusion of pregnancy so as to restore blood flow.

SUMMARY

It would be desirable to be able to target a specific site in a trauma patient's vasculature at which to place a temporary occlusion device. The present invention provides temporary occlusion devices and techniques that can be deployed percutaneously to temporarily occlude blood vessels including major blood vessels (e.g., arteries) as well as armies within organs until specialized care can be obtained to surgically control massive hemorrhage following civilian or military trauma. The temporary occluders of the present invention may be used as an internal tourniquet focused on a specific target region or vessel as an alternative to a conventional tourniquet to control major extremity bleeding following trauma. The temporary occluders of the invention providing a more effective, reliable and highly targeted method to control major blood vessel hemorrhage. Furthermore, unlike a conventional tourniquet, the temporary occluder of the present invention may be used even in the presence of soft tissue injury. Once deployed, minimal post-deployment supervision is required during the time required to transport the patient to the specialized care required to surgically repair the damaged blood vessel.

In accordance with the invention, blood vessels can be occluded using a pair of cooperating occluder elements or, in some embodiments, occluders with only a single occluding element. In one embodiment of a two-part occluder, the damaged blood vessel is accessed with a delivery tube, such as a needle that is pre-loaded with the occluder; typically, this is within the level of skill of the average first provider such as a military medic or civilian emergency medical technician (EMT). Ultrasound may be used to identify and access a precise target site on the damaged blood vessel where the occluder is to be placed, although other techniques (e.g., tactile sensing) may be employed to sense the presence of a vessel, tubular or target structure. Ideally, the occluder may be placed upstream of the location of the hemorrhage, although in some instances it may be desirable to also place an occluder at a downstream location to prevent other feeder vessels from directing blood flow to the hemhorrage site. In the case of a two-part occluder, deployment involves passing a distal occluder element across the blood vessel (e.g., artery) so that a distal element is disposed adjacent or against the outer surface of the blood vessel on the far (distal) side of the blood vessel, and then positioning a proximal occluder element adjacent or against the outer surface of the blood vessel on the near (proximal) side of the blood vessel, or against the outside surface of the skin. The degree of occlusion can be varied between full occlusion or partial occlusion by varying the degree to which the proximal and distal occluder elements are urged toward or away from each other. Once deployed, removal of the temporary occluder may be performed in the specialized care center at the appropriate time, after or during surgical treatment for the injury. Following removal of the temporary occluder, hemostasis of the punctures caused by deployment of the temporary occluder across the blood vessel may be obtained with standard manual compression of the blood vessel, thus minimizing the need for further blood vessel repair.

Alternatively, other means such as cauterization of the tissue, deploying a polymeric sealant, or deploying gauze or a pad, or positioning a coated stent in the vessel, may be used to arrest blood flow.

In some embodiments of the invention, the occluder may have only a single occluding element that can be positioned with respect to a target site on the blood vessel so that pressure applied to the occluding element can be transferred to the blood vessel, either directly or through intervening tissue, sufficiently to cause partial or full occlusion of the vessel.

DRAWINGS

The various objects and advantages of the invention will be appreciated more fully from the following description, with reference to the accompanying drawings in which:

FIG. 16 is a series of three photographs of a simulated tubular vessel showing how the occluder with interdigitated legs constrains the vessel in a serpentine configuration to occlude the vessel;

FIG. 19 is an illustration of the control handle and controls as the device is advanced to penetrate the blood vessel;

FIG. 20 is an illustration of the control handle and controls as the distal occluder is deployed out of the needle;

FIG. 21 is an illustration of the control handle and controls as the distal occluder is engaged with a distal wall of the blood vessel;

FIG. 22 is an illustration of the control handle and controls as the needle is retracted to deploy the proximal occluder;

FIG. 23 is an illustration of the control handle and controls as the occluders are brought together to partially occlude the blood vessel;

FIG. 24 is an illustration of the control handle and controls as the occluders are brought together to fully occlude the blood vessel;

ILLUSTRATIVE EMBODIMENTS

Figure 1:
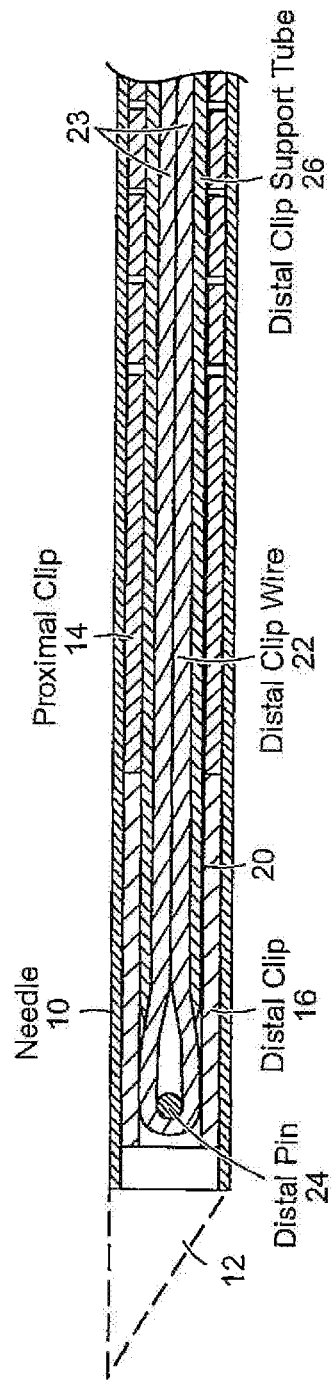
FIG. 1 is a longitudinal sectional illustration of the distal region of an embodiment of a two-part occluder contained in a delivery needle.
Figure 2:
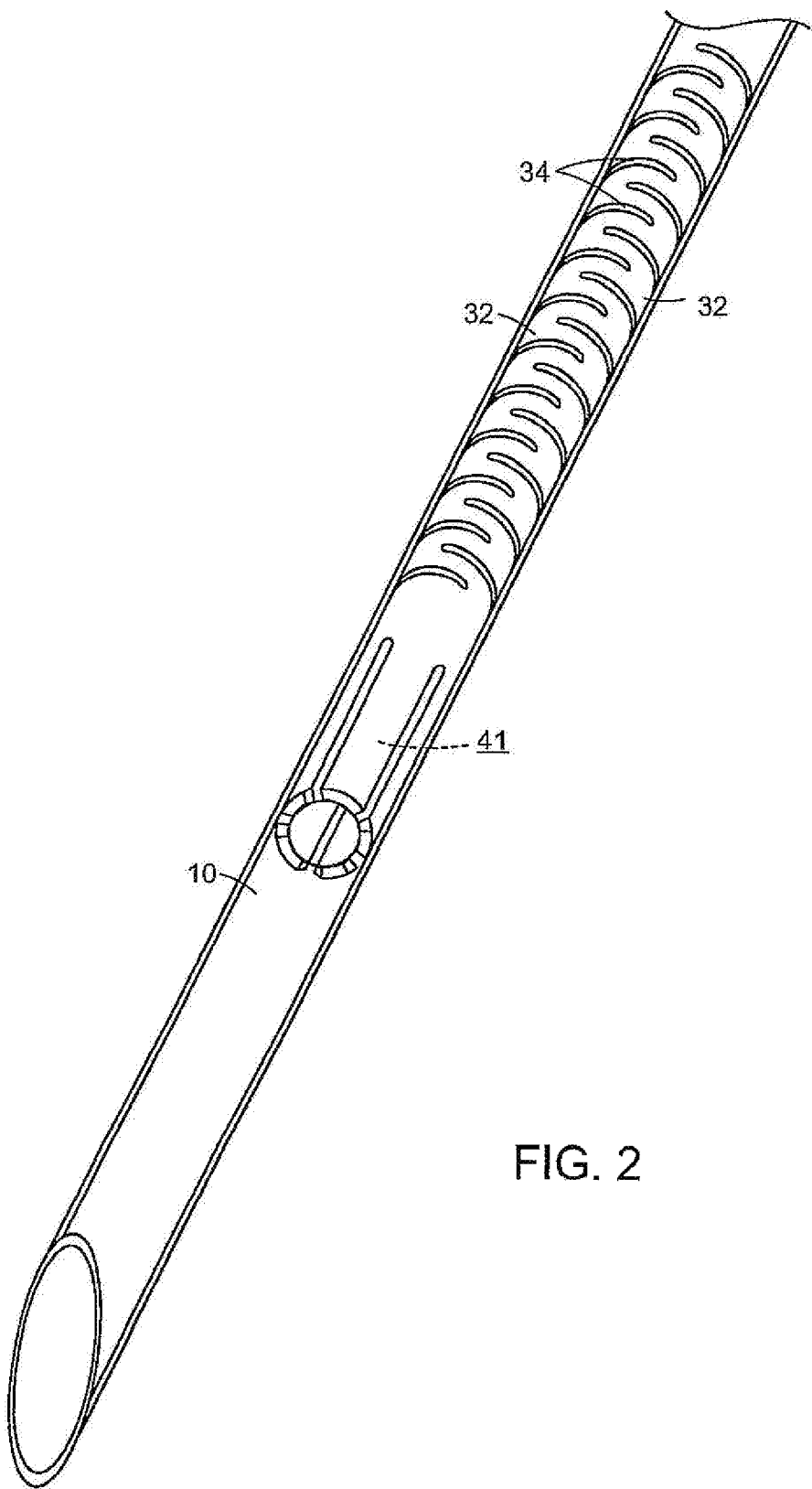
FIG. 2 is an illustration of the needle containing a flexible shaft with a proximal occluder at the distal end of the shaft and the legs of the occluder in a radially contracted position.

FIGS. 1-6 illustrate one embodiment of a two-piece temporary occlusion device that can be inserted percutaneously through tissue to a target site of a blood vessel, upstream and, in some cases, downstream of a hemorrhaging site. The device includes separate proximal and distal clips (occluders) that are containable, in tandem, within the lumen of a delivery tube, such as a needle 10 having an outlet opening 12 at its distal end. Each of the proximal and distal occluders is capable of self-expanding from a low-profile configuration in which it can be releasably contained in the needle 10 and a diametrically expanded configuration when it is ejected from the needle. FIG. 1 illustrates the components of the distal end of one embodiment of the device that includes the needle 10 containing the occluders in readiness to be deployed by being advanced out of the distal opening 12 of the needle. The occluders in this embodiment comprise a proximal occluder 14 and a distal occluder 16. The occluders can be deployed separately and independently on opposite sides of the traumatized vessel and can be urged together to controllably urge the vessel walls together to fully or partially occlude blood flow and prevent or control blood loss from the damaged vessel.

Figure 6:
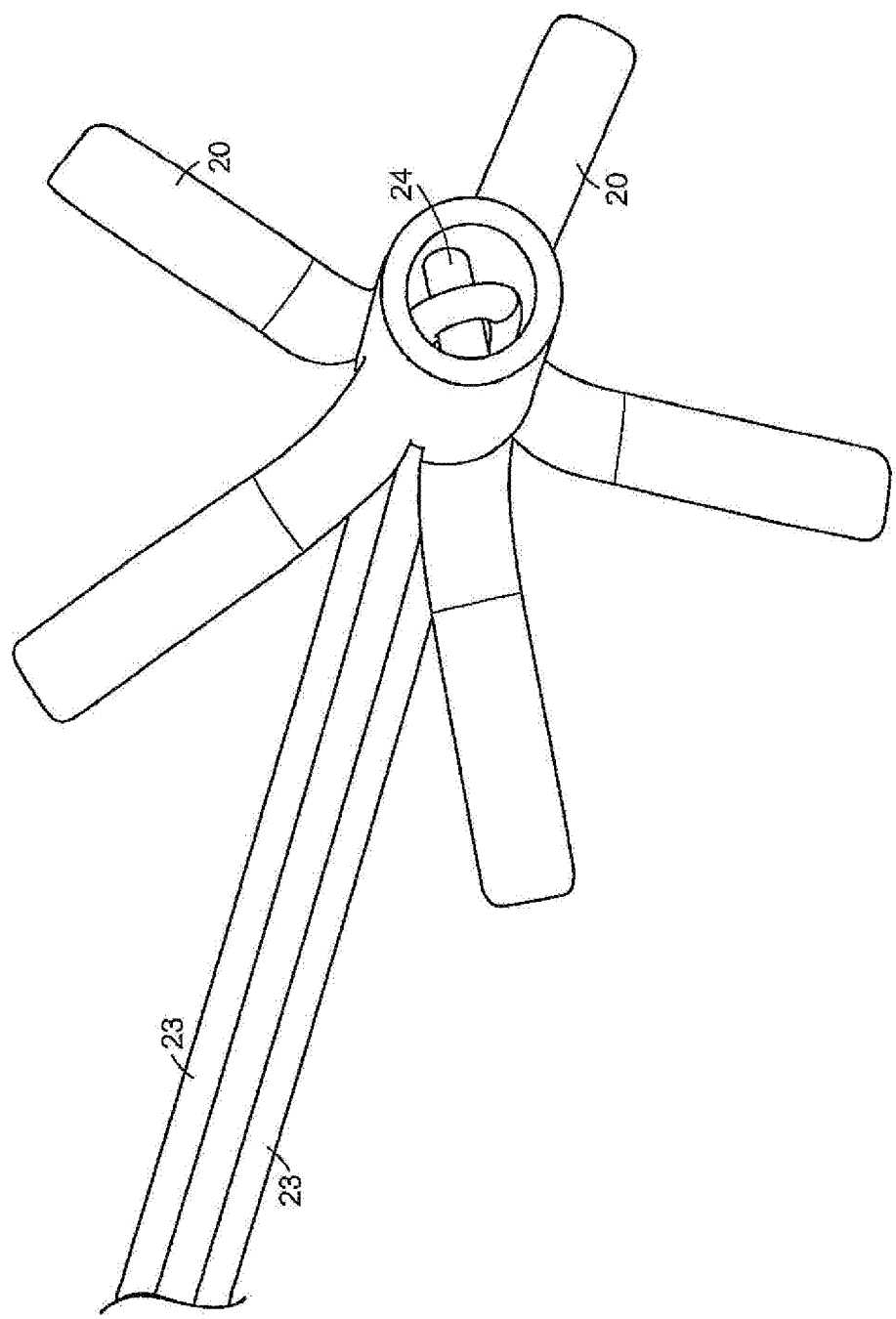
FIG. 6 is an illustration of the distal occluder assembly with its legs in radially extended position.

The distal occluder 16 of this embodiment may be formed from a shape memory material such as Nitinol and may have a tubular body 18 and a plurality of legs 20 that, when in the deployed, expanded-diameter configuration, extend radially from the body 18. In some instances, the distal occluder may be made of a nitinol wire that may be shaped to form loops or other shapes that define radially expandable elements when deployed out of the needle. The distal occluder 16 is contained in the needle with its legs constrained in a stressed, low profile configuration in which the legs 20 extend in a proximal direction. The shape memory of the distal occluder may be such that when released from the delivery tube and unstressed, the legs self-extend radially outward to assume a configuration as shown in FIG. 6. The distal occluder also is releasably attached to a distal occluder wire 22 or filament that extends proximally through and out of the proximal end of the needle 10 to a proximal location where it can be controlled by the medic or EMT. In this illustrative embodiment the wire 22 may be attached to the distal occluder by passing the wire 22 about a pin 24 that is secured to and extends transversely through the tubular body 18 of occluder 16. The device also may include a distal occluder support tube 26. The wire 22, passed about the pin 24 forms two wire tails 23 that extend proximally through the support tube 26 and out of the proximal end of the tube 26. The proximal ends of the wire tails 23 may be attached to a control handle as described further below.

The distal support tube 26 may have a rigid segment 28 at its distal end 28 and may have a longer, flexible proximal portion 30 that can be controlled by the EMT by manipulating a handle at the proximal end of the device, described below. The support tube may be formed from Nitinol, or other suitable material and may have segments 32 defined by transverse cuts 34 formed on alternating sides and at spaced intervals along the length of the proximal portion that provide the flexibility while also enabling the support tube to have an adequate degree of column strength as well as to provide some torsional stiffness. The support tube 26 is dimensioned so that its distal tip can fit into the tubular body 18 of the distal occluder 16. The distal tip of the rigid portion 28 of the support tube 26 may be formed to include a pair of diametrically opposed slots 36 adapted to receive the transverse pin 24 to enable the rotational position of the distal occluder to be adjusted by rotating the support tube 26 from its proximal end that is controllable by the EMT, as described below. The distal end of the support tube also may include another pair of diametrically opposed slots 38 to receive portions of the bight of the wire 22 if the wire 22 is formed from a material that may bulge slightly outwardly after being wrapped around the pin (FIG. 1). Other arrangements may be provided for releasably attaching a wire, filament or other elongate member to the distal occluder.

The proximal occluder 14 (FIG. 2) may be formed as an integral part of a proximal occluder tube 40. The tube 40 may be constructed with transverse slits formed along the length of a proximal portion of tube 40, similarly to those on the distal occluder support tube 26, so that it is flexible and has adequate column strength. The distal occluder support tube 26 is slidably contained within the lumen of the proximal occluder tube 40. The proximal occluder 14 and proximal occluder tube 40 may be formed from a unitary tube of Nitinol or other material having shape memory characteristics. The proximal occluder 14 is located in the delivery needle in tandem behind the distal occluder 16 and is formed so that it is contained in the needle 10 with its legs 41 constrained in a low profile and extending distally in readiness to self-deploy to a radially extended configuration when advanced out of the distal end of the needle 10.

Desirably, the needle 10 may be no greater than about 17 or 18 gauge. By way of example, the needle may have an outer diameter of 1.8 mm and an inner diameter of 1.17 mm Each of the proximal and distal occluders 14, 16 and the proximal occluder tube 40 may have an outer diameter of 1.07 mm or less and an inner diameter of 0.77 mm or less. The pin 24 may have a diameter of 0.30 mm. The distal occluder support tube 26 may have a outer diameter of 0.70 or less and an inner diameter of 0.50 mm or less.

Figure 7:
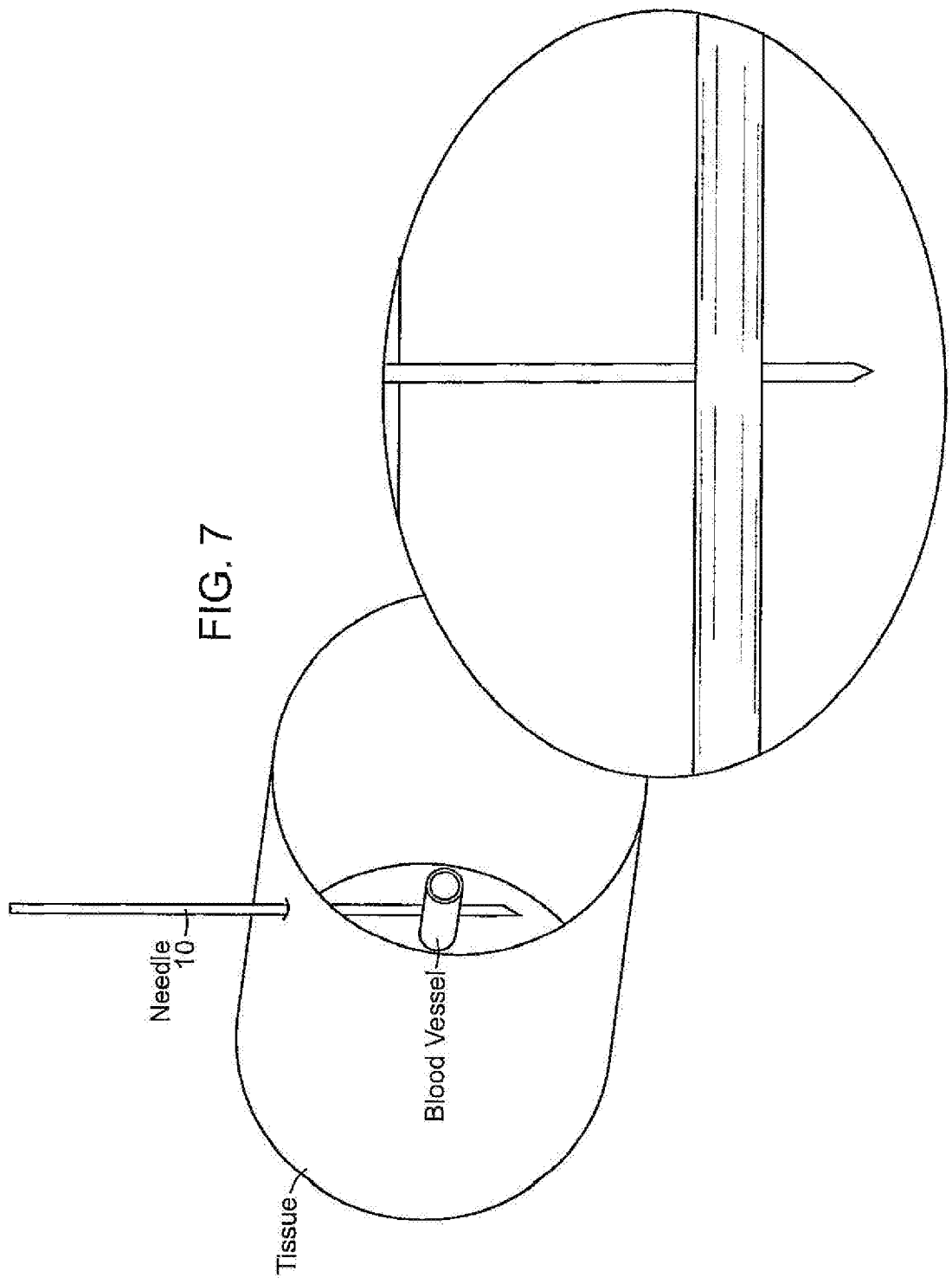
FIGS. 7-12, 13A and 13B illustrate, diagrammatically, a procedure for using the embodiment of FIGS. 1-6 of the invention to occlude or control blood flow from a traumatized blood vessel.
Figure 8:
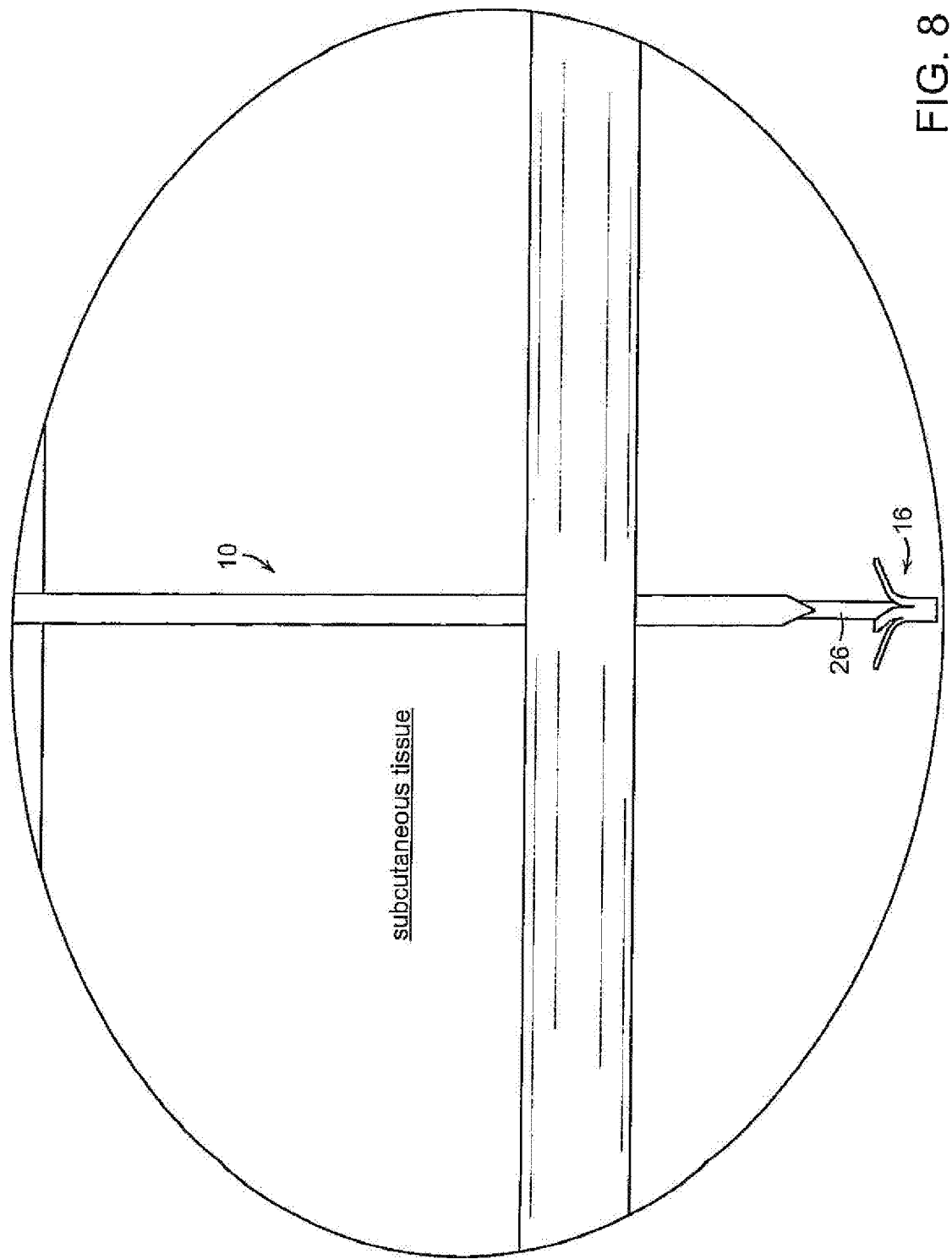
Figure 9:
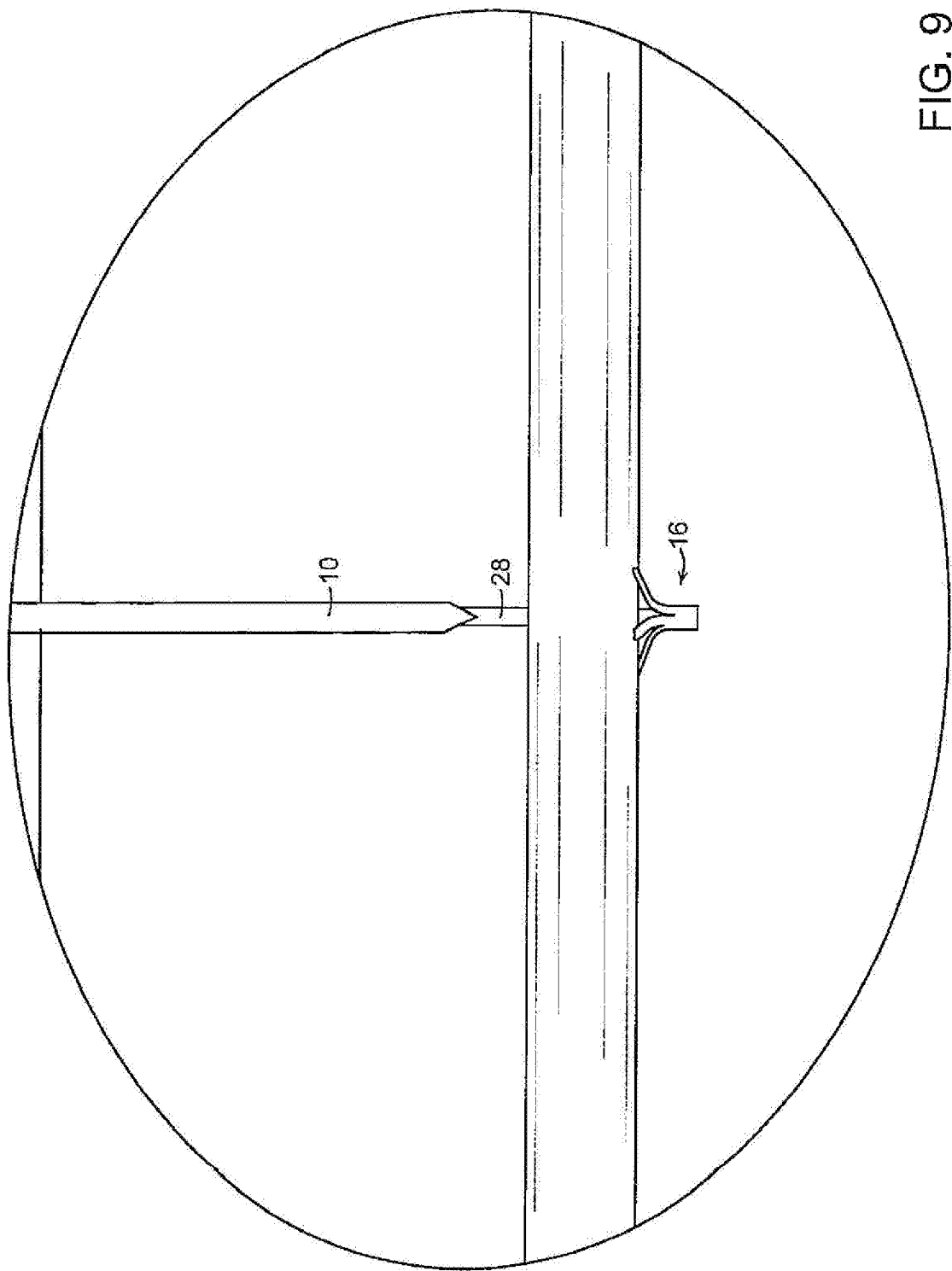
Figure 10:
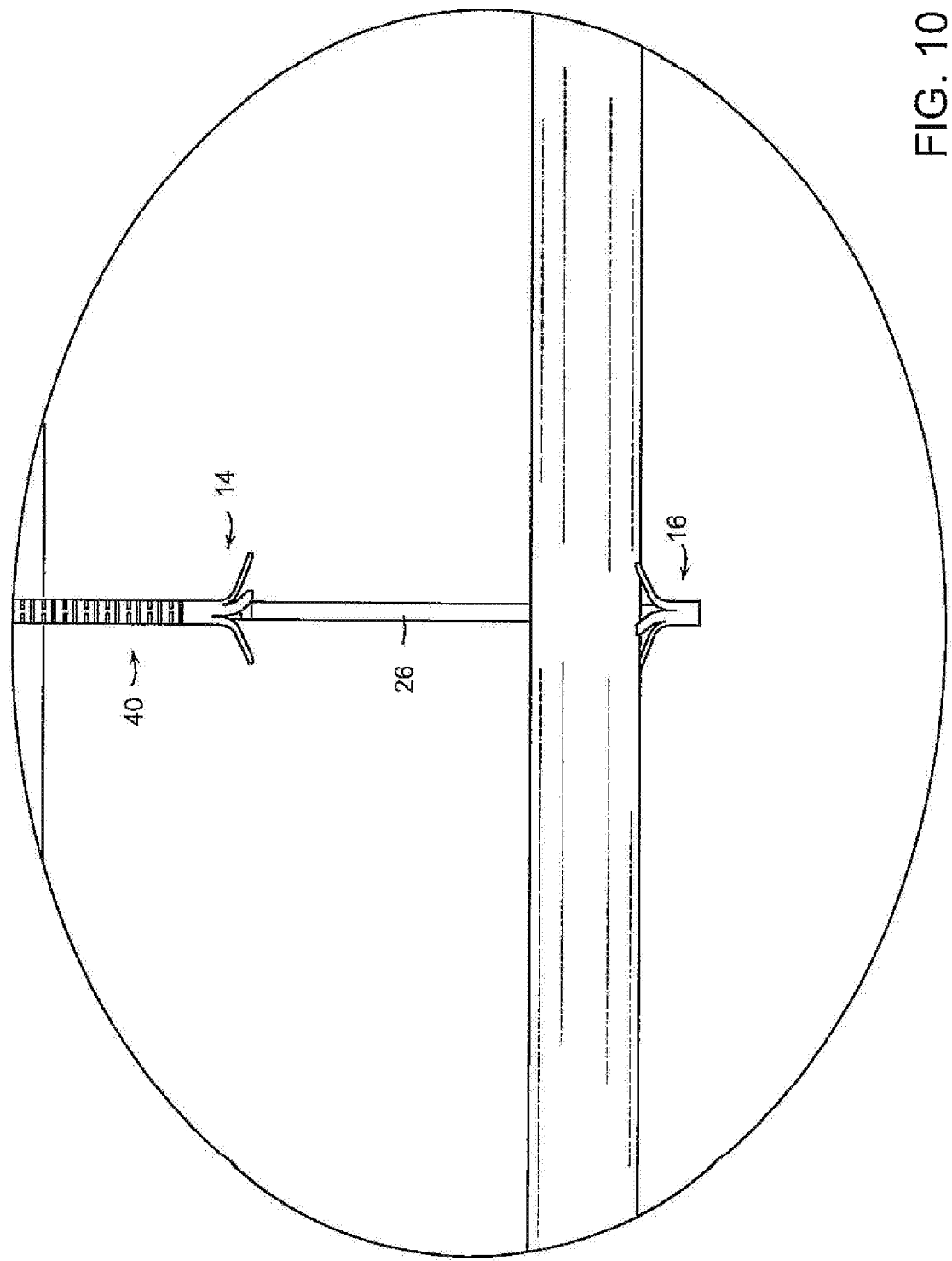
Figure 11:
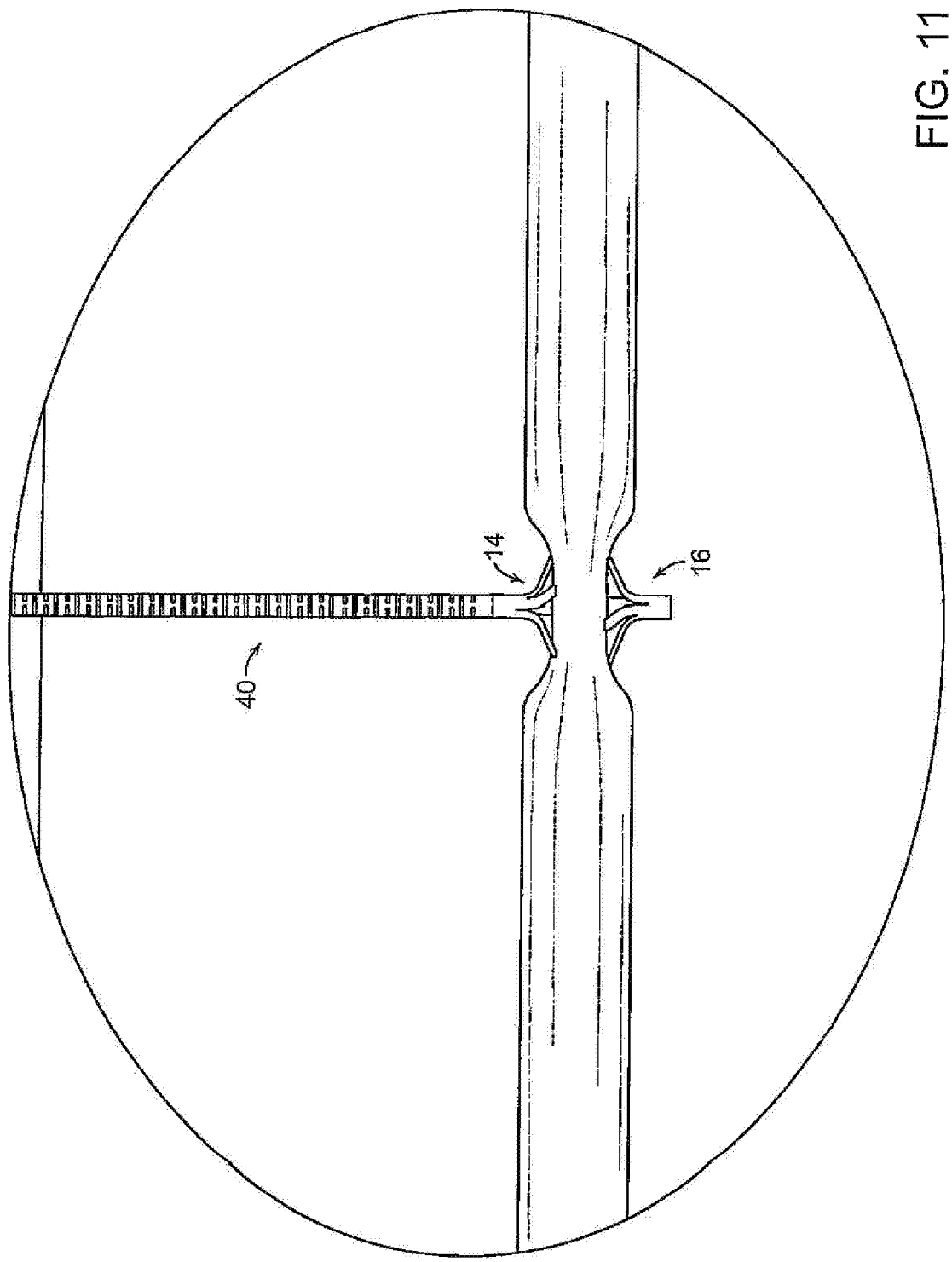

One manner in which the device may be used to control blood flow or to occlude the injured vessel is illustrated, diagrammatically, in FIGS. 7-14. A portable ultrasound device may be utilized to visualize the vessel to facilitate placement of the needle and occluders. As shown in FIG. 7, the needle, loaded with the device, may be passed percutaneously through the skin and subcutaneous tissue to and through the injured vessel upstream of the site of hemorrhaging to transfix the opposing walls of the blood vessel. With the distal tip of the needle on the distal side of the vessel, the distal support tube 26 is advanced distally to urge the distal occluder 16 out of the needle 10, thus enabling the legs 20 of the distal occluder to self-expand to their radially extended positions (FIGS. 8 and 20). The distal occluder support tube 26 and tails 23 of the wire 22 then are drawn proximally to bring the deployed legs of the distal occluder 16 into engagement with the distal wall of the blood vessel (FIGS. 9 and 21). The needle 10 then is drawn proximally over the tube 40 to expose the proximal occluder 14 and enable the legs 41 of the proximal occluder to self-expand to their radially extended, deployed configuration on the proximal side of the blood vessel, tubular structure or other target organ (e.g, the liver) (FIGS. 10 and 22). The proximal tube 40 then is advanced distally to urge the proximal occluder 24 toward the distal occluder so that the occluders 24, 16 cooperate to compress the opposing walls of the blood vessel together to occlude the blood vessel (FIGS. 11, 22 and 23) to a controllable degree dependent on the extent of compression. In cases where a solid organ is hemhorraging it may ber necessary to two or more occlusion devices to control blood loss.

It is advantageous, in the case of traumatic injury to a blood vessel, particularly a major blood vessel, to minimize the risk of complete blood stagnation that could lead to clot formation. To that end, the device enables the medical personnel to control the degree of vessel occlusion by varying intermittently the degree of occlusion applied to the vessel. By varying the tension on the wire 22 and the position of the proximal tube 40 and proximal occluder 14, the degree of blood flow out of the vessel can be balanced sufficiently with the degree of occlusion to avoid clot formation while minimizing blood loss until the patient can be transported to a facility where the special care to treat the trauma is available. The device then can be removed by withdrawing wire by pulling on one of the tails, withdrawing the proximal tube 40 and occluder 14 into the needle to collapse the occluder legs to a low profile and withdrawing these components and the distal support tube 26 from the patient. The distal occluder 16 may be left in place or, if the remedial surgery to treat the trauma made the distal occluder easily accessible, the distal occluder may be removed as well. The distal occluder 16 also may be formed from a biodegradable material to be absorbed by the body over time.

Also, among the advantageous features of the foregoing illustrative embodiment of the invention is the manner in which the proximal and distal occluders may cooperate to occlude the vessel in a relatively atraumatic manner that reduces the risk of further damage to the vessel. The occluders are configured so that when they are deployed they can be oriented so that the legs 20, 41 of the distal and proximal occluders 16, 14 are out of registry with each other and also are interdigitated with each other. The distal occluder support tube 26 is formed to be able to transmit torque to the distal occluder 16 by the connection of the tip slots 36 with the pin 24, thus enabling rotation of the distal occluder 16 to assure that the proximal and distal legs are out of registry. The unstressed configuration of the occluders is designed so that when the occluders are brought toward each other, the out-of-registry proximal and distal legs can interdigitate or approach interdigitation sufficiently to tend to constrain the walls of the blood vessel in a serpentine pattern as suggested, diagrammatically, in FIGS. 14 and 15.

Figure 14:
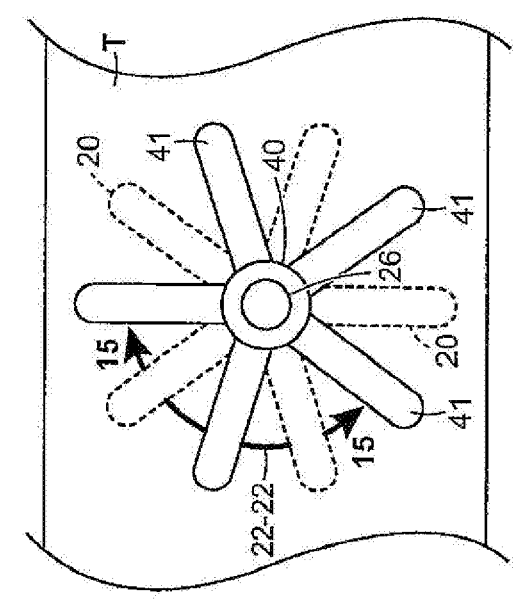
FIG. 14 is a diagrammatic plan view of the two-occluder device in which the legs of the proximal and distal implants are in engagement with the proximal and distal walls of tissues T, such as the walls of a blood vessel.
Figure 15:
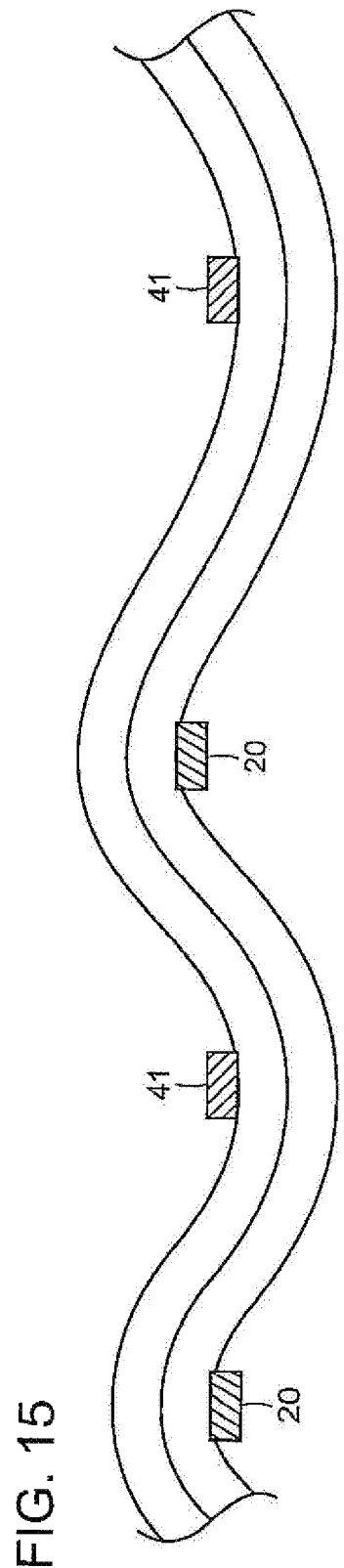
FIG. 15 is a diagrammatic sectional illustration as seen along the circumferential line 15-15 of FIG. 14 showing the manner in which the interdigitated legs 20, 41 of the occluders are oriented and the manner in which the interdigitated legs constrain the tissue layers in a series of sequential, alternating and reversing serpentine bends.
Figure 17:
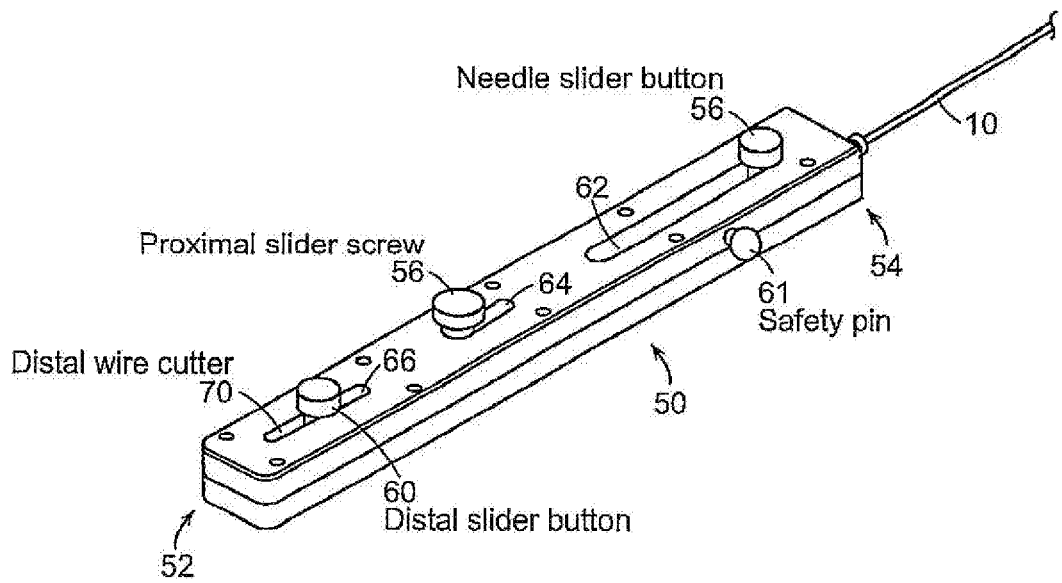
FIG. 17 is an illustration of a control handle for operating the device.
Figure 18:
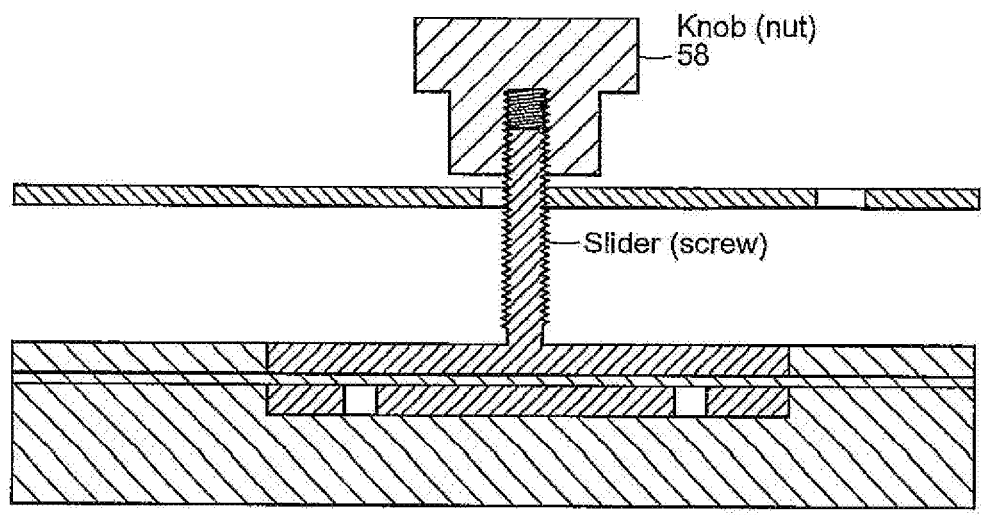
FIG. 18 is a cross sectional illustration of the proximal slider control and its connection to the proximal tube.
Figure 25:
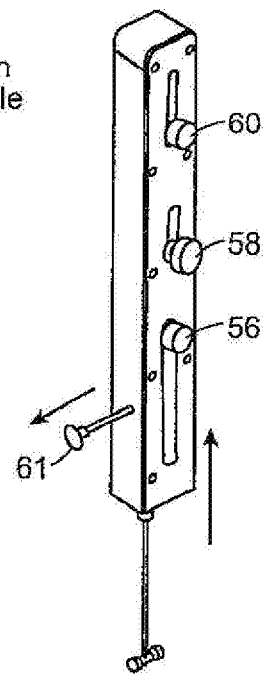
FIG. 25 is an illustration of the control handle and controls as the safety pin is withdrawn and the needle is retracted fully to enable the device to be folded against the patient.
Figure 26:
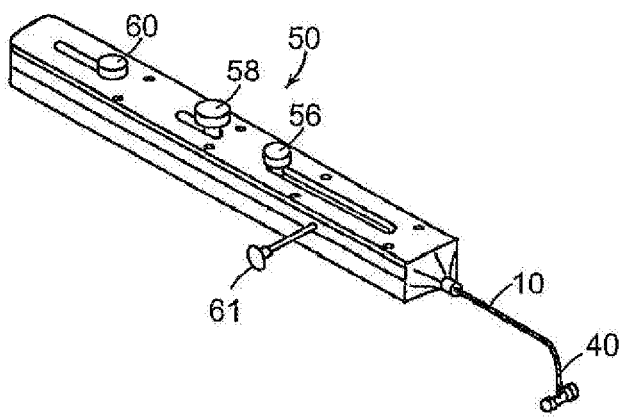
FIG. 26 is an illustration of the control handle and controls when the needle has been fully retracted and the device has been folded to place it against the exterior of the patient.
Figure 27:
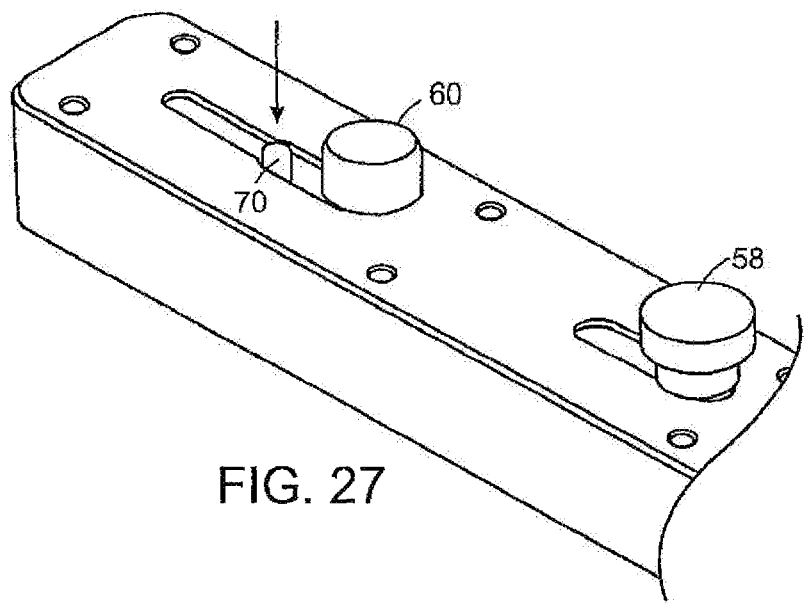
FIG. 27 is an illustration of the control handle and controls when detaching the deployment components for removal from the patient.

FIGS. 14 and 15 illustrate an arrangement of the legs 41, 20 of the proximal and distal implants in which the legs are interdigitated so that they do not effect a direct compressive clamping of the tissue but, instead, engage the tissue to constrain the tissue in a serpentine configuration extending at least partly about the axis of the occluder in a generally circumferential direction. In this arrangement, the legs of one of the implants are out of registry with those of the other implant so that when viewed in plan, the legs of one implant lie between the legs of the other. In this configuration the opposing walls of the vessel are together partially wrapped about the legs 20, 41 in alternating directions to constrain the tissue in a serpentine configuration as seen diagrammatically in FIG. 15. The legs of one or both of the occluders may be formed to extend at an acute angle to the occluder axis to define a conical configuration. This provides an additional means by which the clamping forces can be adjustably controlled. By selecting, during manufacture, a particular cone angle defined by the expanded legs as well as their stiffness, the characteristics of the serpentine pattern can be determined.

FIG. 16 shows three photographs of folds formed in a simulated blood vessel and those folds or ripples extend radially beyond the ends of the legs 20, 41, effectively extending the radial extent of the closure and defining a circumferential band with a diameter greater than that of the occluders. By way of example but not limitation, a two-part occluder as described above and having legs that define a diameter of 5.5 mm may be able to occlude vessels that are over 7 mm (and even equal or greater than 1 cm) in diameter. The ability of the two-occluder occluder to cause serpentine ripples beyond the diameter of the legs 20, 41 of the device enables the device to be at least partly effective and, possibly fully effective, even if the needle misses and does not transfix the vessel but is sufficiently close to the vessel so that some of the legs, or at least some of the circumferential band defined by the serpentine ripples overlies at least a portion, and possibly all, of the width of the vessel.

FIGS. 17-27 illustrate, somewhat diagrammatically, a control handle 50 by which the deployment of the above-described device may be facilitated. The control handle has a housing 51 with proximal and distal ends 52, 54. The proximal ends of each of the needle 10, distal occluder support tube 26 and proximal occluder support tube 40 are contained telescopically within the housing, with the rigid needle being outermost and containing tube 26 that, in turn, contains the tube 40. The proximal end of tube 26 extends proximally beyond the proximal end of the needle and the proximal end of the tube 40 extends proximally beyond the proximal end of the tube 26. Proximal portions of each of the needle 10, tube 26 and tube 40 are connected to sliding controls 56 (connected to the needle), 58 (connected to the proximal occluder support tube 26) and 60 (connected to the distal occluder support tube 40), respectively, each of the controls 56, 58, 60 protruding out of the housing through respective, longitudinally extending slots 62, 64, 66. Sliding control 58 preferably includes a threaded button 64 (see FIG. 19) by which the position of the control 58 can be secured by tightening the button to press against the outer surface of the handle. The tails of the filament 22 extend proximally through the proximal occluder support tube to a location within the handle, proximally of tube 40, at which the tails are secured to the housing.

Figure 12:
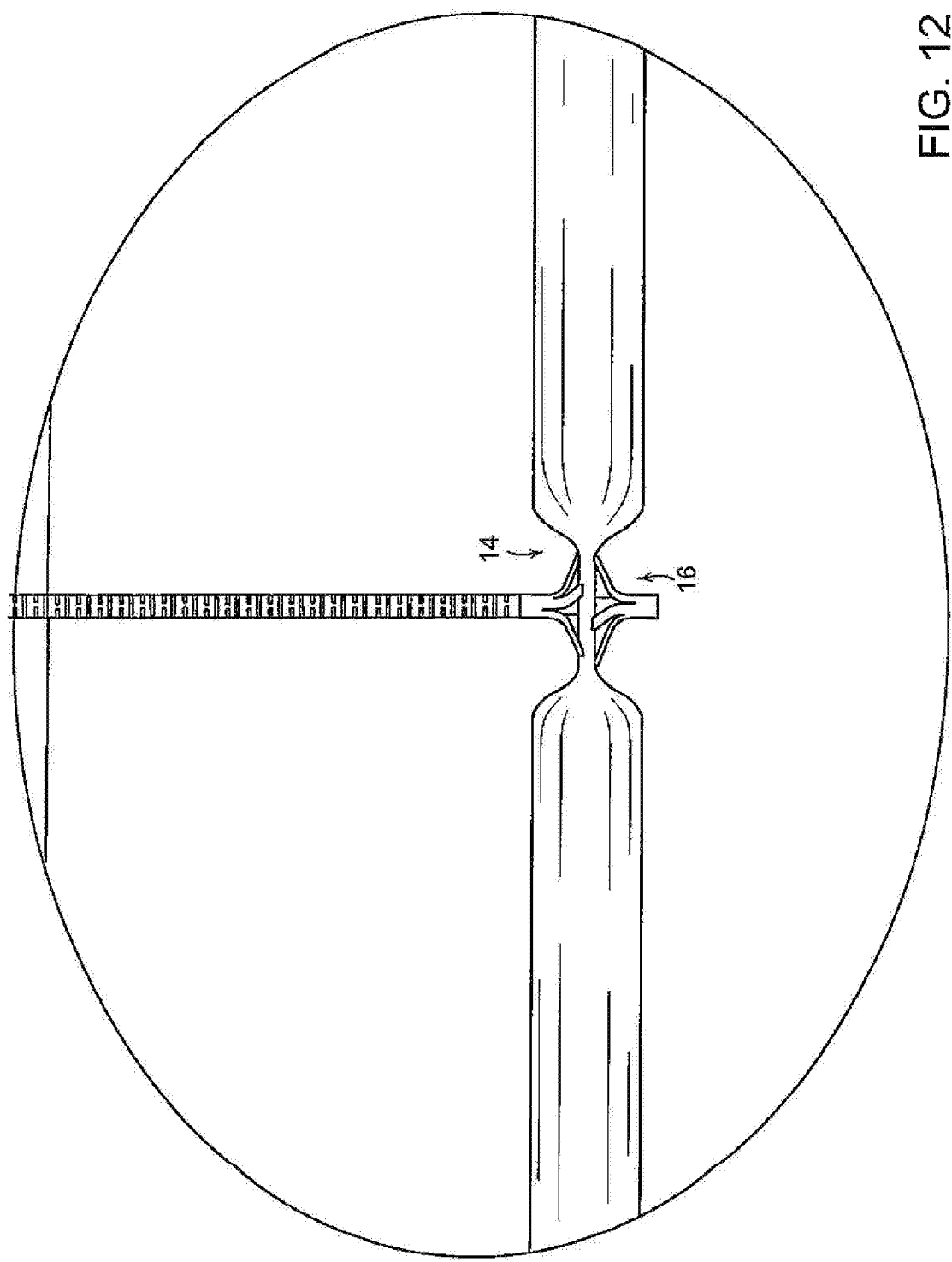
Figure 13A:
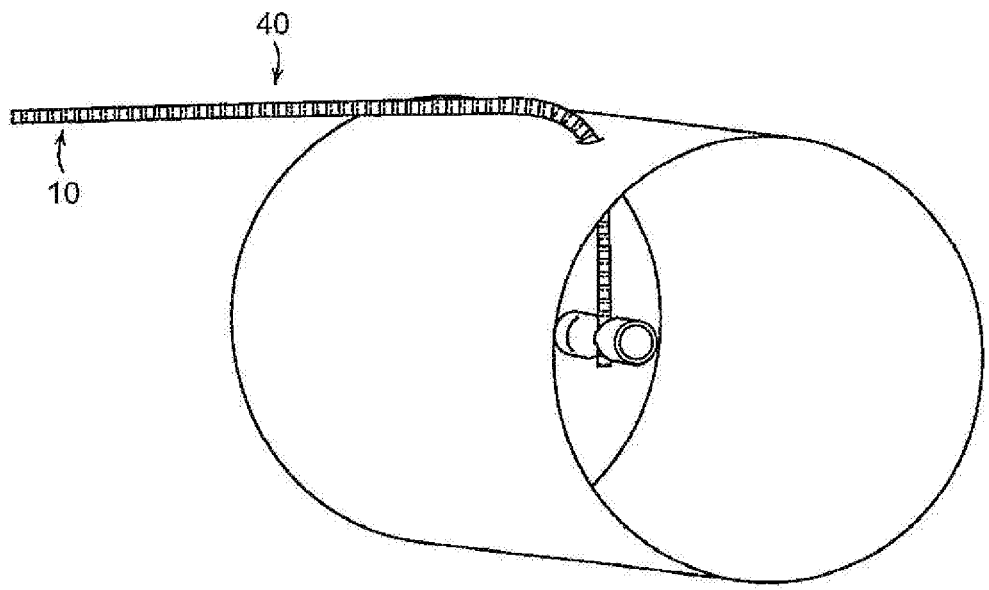
Figure 13B:
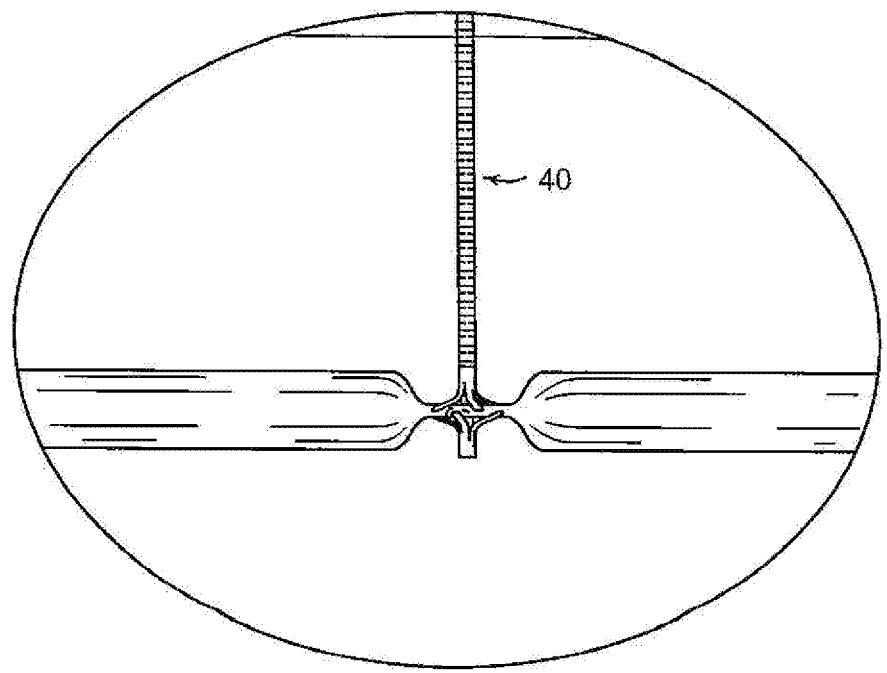

The control handle is operated as shown in FIGS. 12-27. As shown in FIG. 12, with the needle extending distally from the handle, the needle is advanced through the skin and subcutaneous tissue to transfix the blood vessel and to position the distal tip of the needle distally of the vessel, as described above. The distal occluder control 60 then is slid distally through the slot 66 to cause the tube 26 to push the distal occluder 16 out of the distal end of the needle to enable the legs of the distal occluder 16 to self-expand to their deployed configuration distally of the vessel (FIG. 20). The distal occluder 16 then is drawn proximally into engagement with the distal wall of the vessel by pulling the handle proximally which tensions the filament 22 attached to the distal occluder 16 (FIG. 21). With the distal occluder so deployed, the needle 10 is retracted by sliding control 56 proximally sufficiently to expose the proximal occluder 24 at the end of the tube 40 to enable the legs of the proximal occluder to self-expand (FIG. 22). With the proximal occluder deployed it can be advanced by control to achieve a partial occlusion. It may be noted that the control handle may include a stop member, for example, as a movable pin 61, to limit temporarily the extent to which the proximal occluder can be advanced. If the medic or EMT desires to achieve full occlusion the pin can be disengaged that enables the proximal occluder to ber advanced to achieve full occlusion. The control 58 can be secured in a desired position by tightening the screw 58.

After the medic or EMT is satisfied that a desired degree of occlusion has been established and the device is ready to be secured in position, the needle then is retracted fully to a position outside the patient by sliding the control 56 proximally and with the flexible portions of the tubes 26, 40 extending externally of the patient. The exposed flexible portions of the tubes 26, 40 then can be bent easily (FIG. 26) and secured in an out-of-the-way position, as by taping to the patient. When the device is to be removed, as when the patient has been transported to a facility for further treatment, the connection of the wire to the handle is severed. The handle can include a cutting element 70 such as a button that can be depressed to cause a cutting element within the handle to sever one of the tails 23 of the filament 22. With the filament severed, the entire device can be removed by withdrawing the handle, leaving the distal occluder 16 in place.

It should be noted that, although the invention contemplates piercing the proximal and distal walls of the target vessel to transfix the vessel, sufficient occlusion may be achieved even if the needle does not transfix the vessel, but is sufficiently close to, the vessel. This results from the cooperation of the legs of the proximal and distal occluders by which they constrain the tissue in a serpentine configuration and in which the waviness of the tissue extends radially beyond the diameter defined by the deployed occluder legs. Thus, if the occluders are deployed closely adjacent the target vessel legs may overlie the vessel or the waviness of the tissue may extend beyond the diameter of the occluder legs and may encompass the region of the target vessel to be occluded. The invention thus provides a margin of error and may enable sufficient temporary occlusion to be achieved even if the target vessel is not transfixed by the needle.

Figure 3:
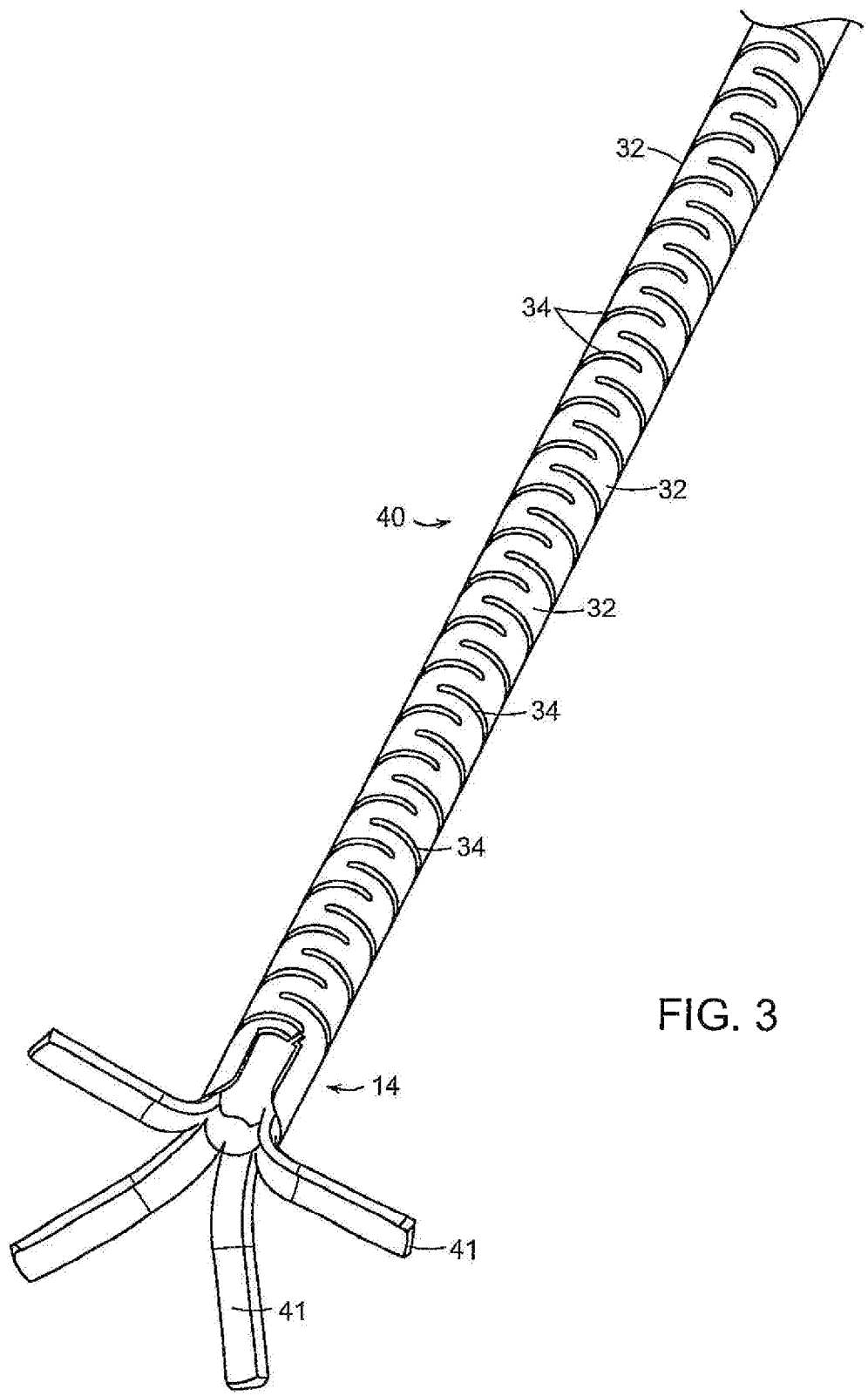
FIG. 3 is an illustration of the flexible shaft with the legs of the distal occluder expanded in their radially deployed positions.
Figure 4:
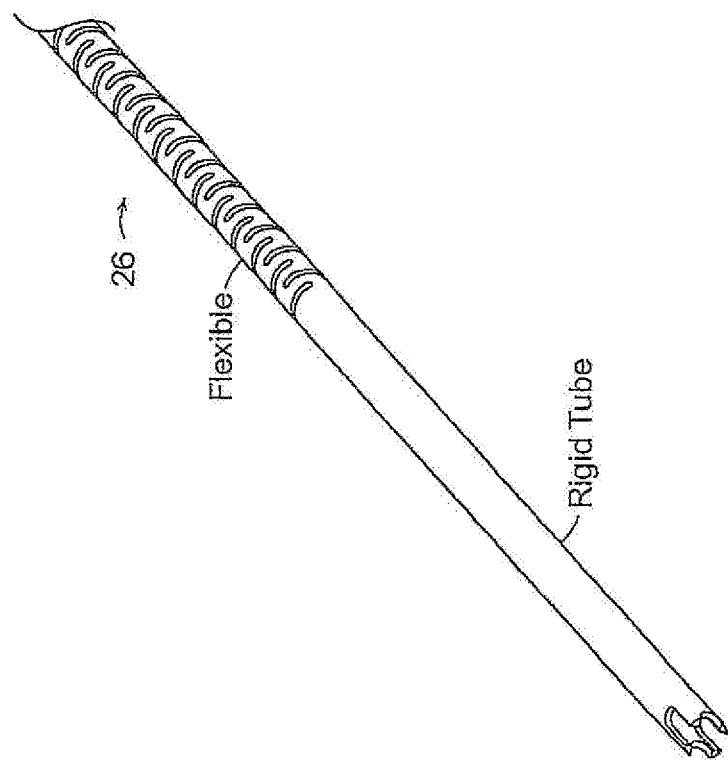
FIG. 4 is an illustration of the distal portion of the distal occluder support tube.
Figure 5:
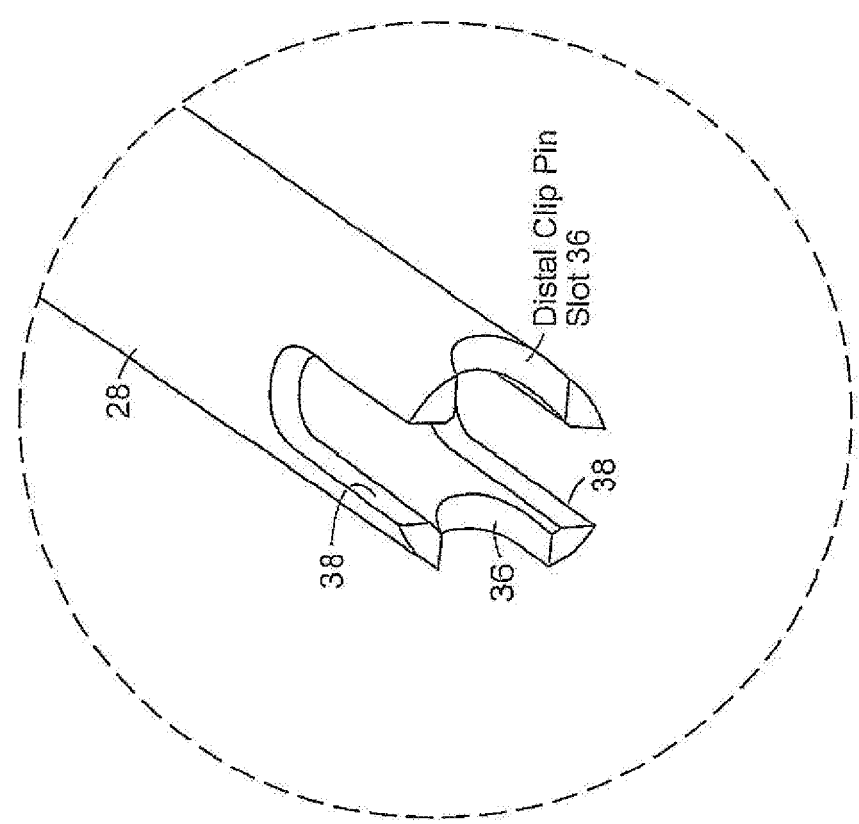
FIG. 5 is an enlarged illustration of the distal end of the distal occluder support tube.

In a further aspect of the invention, a traumatized blood vessel also may be occluded with a simplified one-occluder device that comprises a needle that contains a proximal occluder 14 attached to a proximal support tube 40 as shown in FIG. 3. With this embodiment the needle, support tube 40 and proximal occluder 14 can be advanced through subcutaneous tissue toward the blood vessel to position the needle tip proximally of the vessel. The support tube 40 then can be advanced (or the needle retracted) to deploy the proximal occluder 14 out of the needle, enabling the legs 41 to expand. The support tube 40 then can be urged distally to cause the legs of the occluder to apply a compressive force through any intervening subcutaneous tissue and to the blood vessel, causing compression and partial or, possibly, complete occlusion of the vessel. In this simplified embodiment the proximal occluder may take alternate forms that can have a low profile containable in a hollow delivery needle and an expandable form having an effective larger transverse dimension capable of applying a compressive force to an area of tissue, such as a blood vessel, or subcutaneous tissue adjacent a blood vessel. The degree of compressive force can be varied by the medical attendant to balance blood loss with occlusion. After the patient has been transported to a medical facility for treatment, the temporary device can be removed by withdrawing the support tube 40 and proximal occluder back into the needle, causing the legs of the occluder to return to the low profile and then removing the entire device.

FIGS. 28-31 illustrate another embodiment of the invention in which one of the occluder elements is disposed within the patient and a second element is located externally of the patient, with the two elements cooperating to occlude the vessel fully or partially. In this embodiment an elongate cord or filament 70 having proximal end distal ends is provided. The distal end of the cord 70 is securely attached to a distal occluder 72 that may be similar to distal occluder 16 having deployable legs 73, described above, or may take other forms by which it may be configured in a low profile, releasably containable in a delivery tube (e.g., a needle) from which it can be deployed and expanded to a larger diameter. The cord 70 with attached distal occluder 72 is used with a needle 74 that is open at each of its proximal and distal ends 76, 78. The needle may be loaded with the distal occluder 72 by backloading the proximal end 80 of the cord 70 through the opening 78 at the distal end of the needle until the distal occluder has been drawn into the distal end of the needle. The loaded needle then can be advanced percutaneously through tissue and through the target site of the vessel to locate the distal tip of the needle distally of the target site. The needle then is retracted while maintaining the position of the distal occluder until the legs of the occluder have been released from the needle and expanded to their deployed diameter. The position of the distal occluder can be maintained by a tubular pusher that can be advanced over the cord 70 into engagement with the occluder. With the distal occluder deployed, the proximal element of the occluder, which may take any of a number of forms, such as a member 82 with an aperture 84 shown, can be passed over the proximal end of the cord and advanced toward and into engagement with the patient's skin. By manipulating the cord 70 and the proximal element, the degree of occlusion can be controlled by the EMT, medic or other attendant. The proximal element 82 may be provided with a mechanism by which it can be releasably locked to the cord. The position of the distal occluder can be main When the need for temporary occlusion no longer exists (e.g., when the patient has arrived at a surgical facility) the device may be removed simply by pulling the cord while maintaining the position of the needle to draw the deployed occluder back into the distal end of the needle that causes the legs of the occluder to return to their low-profile configuration. The needle together with the occluder then can be withdrawn.

Figure 34:
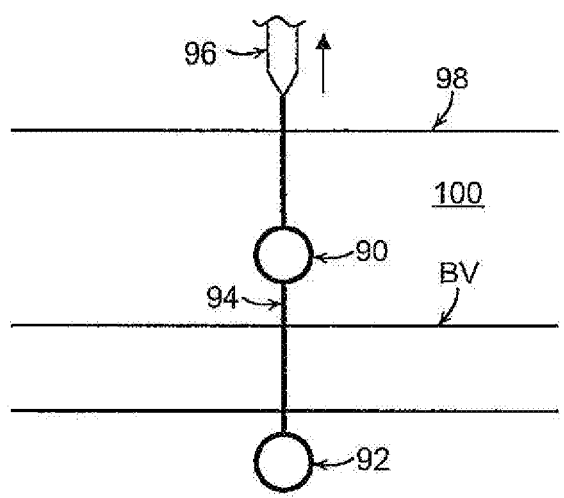
FIGS. 34 and 35 illustrate, diagrammatically, another embodiment of the invention utilizing balloons as the expandable occlusion elements.
Figure 35:
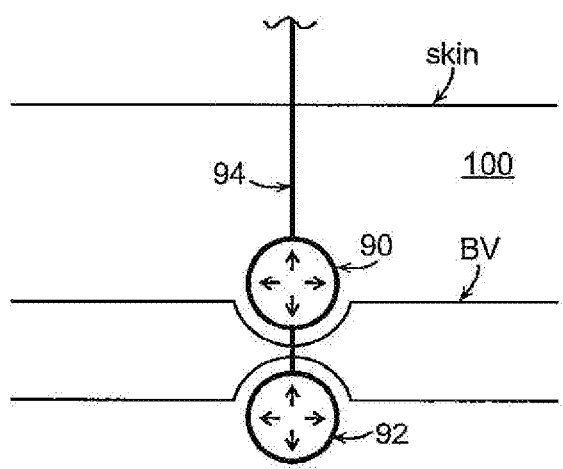

FIGS. 34 and 35 illustrate, diagrammatically, another form of the invention in which the expandable occlusion elements comprise balloons. In this embodiment a pair of balloons 90, 92 may be provided on a common inflation tube 94. The balloons 90, 92 may be formed from any of a variety of materials using techniques well known to those skilled in the art. For example, the balloons may be formed from elastomers (e.g., latex, silicone). The balloons may be spaced in sufficient proximity so that they can be placed to embrace and apply compressive pressure to the blood vessel when inflated. The device may be placed with the aid of a needle or sheath 96 that is advanced percutaneously through the skin 98 and intervening subcutaneous tissue 100 and through or immediately adjacent the vessel to locate the distal end of the sheath or needle distally of the vessel. The needle may be pre-loaded with the balloons and their inflation tube. With the needle positioned through the blood vessel, the inflation tube is advanced through the needle to position the uninflated distal balloon distally of the vessel. The needle then is retracted to expose the uninflated proximal balloon proximally of the vessel (FIG. 34). The balloons then may be inflated together via the inflation tube so that they can compress the vessel between the inflated balloons (FIG. 35). When temporary occlusion is no longer needed, balloons may be deflated via inflation line, and then the two balloons are pulled free of the anatomy by pulling proximally on inflation line.

In another variation of the invention, the balloons 90, 92 may be movable toward and away from each other. In this aspect of the invention each balloon is provided with a separate inflation tube to enable the balloons to be inflated or deflated independently of each other. The inflation tubes are movable longitudinally with respect to each other to enable the deployed balloons 90, 92 to be moved toward and away from each other. With this variation, after the balloons have been deployed proximally and distally of the vessel and the balloons have been inflated, the spacing of the balloons can be adjusted by manipulation of their respective inflation lines so as to vary the degree to which the vessel is occluded.

Figure 28:
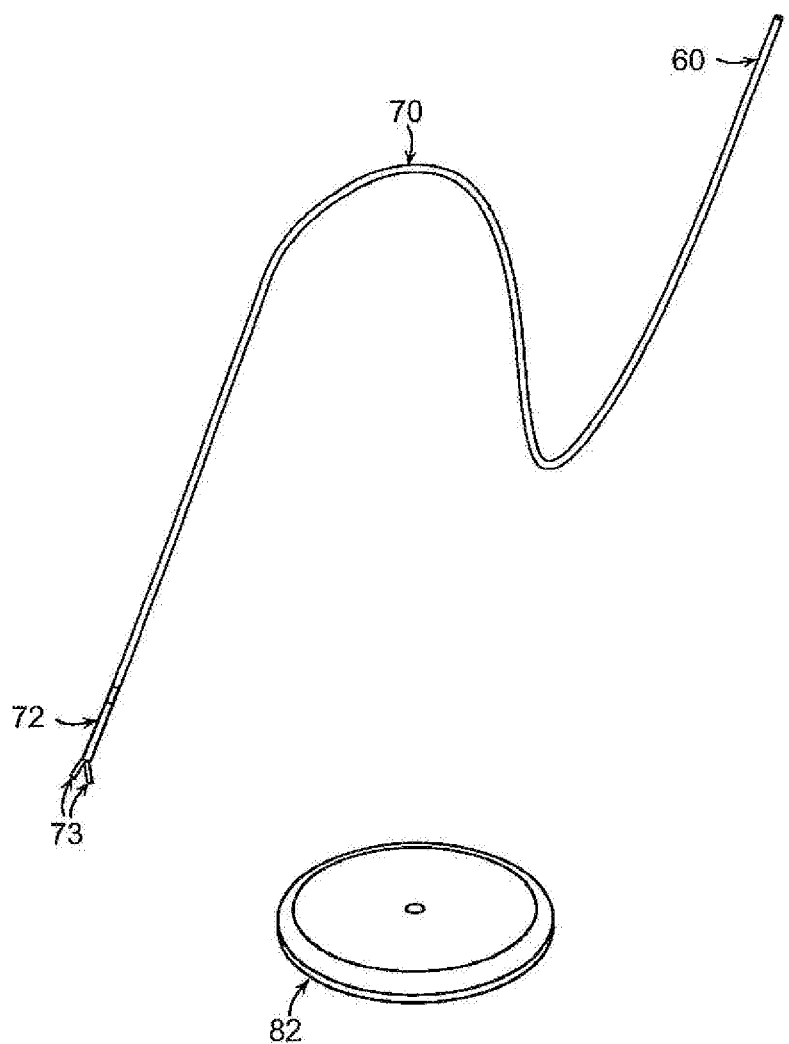
FIGS. 28-33 illustrate, diagrammatically, another embodiment of a temporary occluder.
Figure 29:
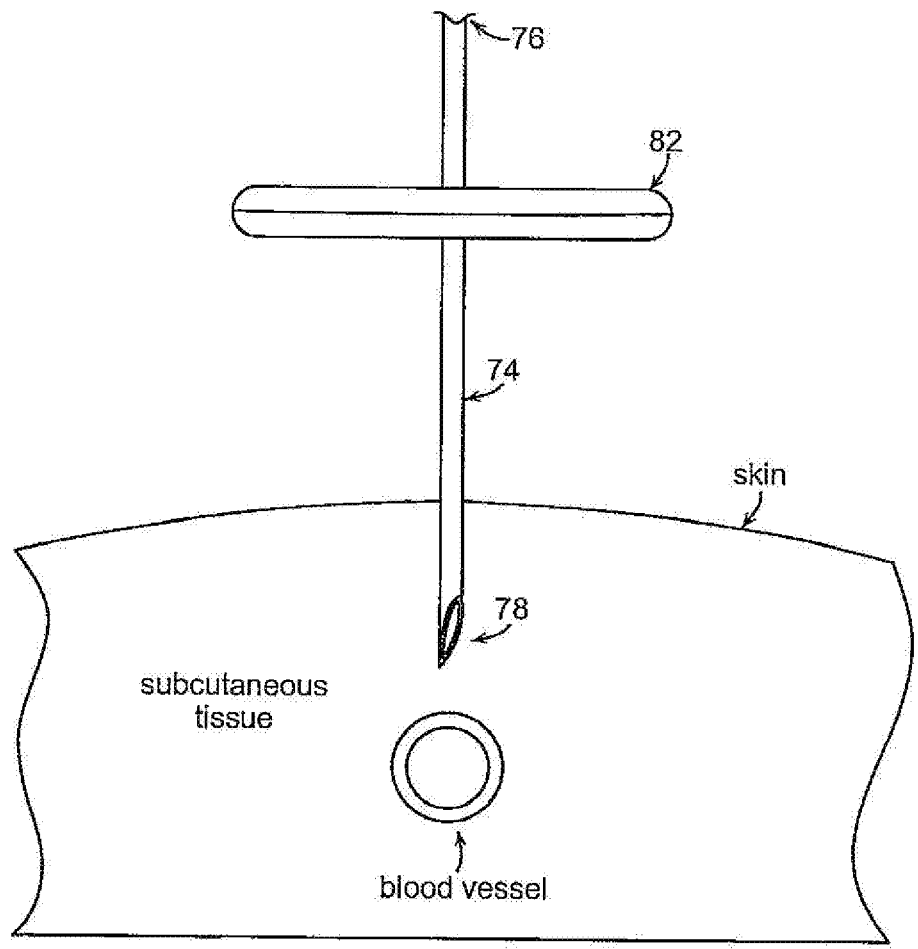
Figure 30:
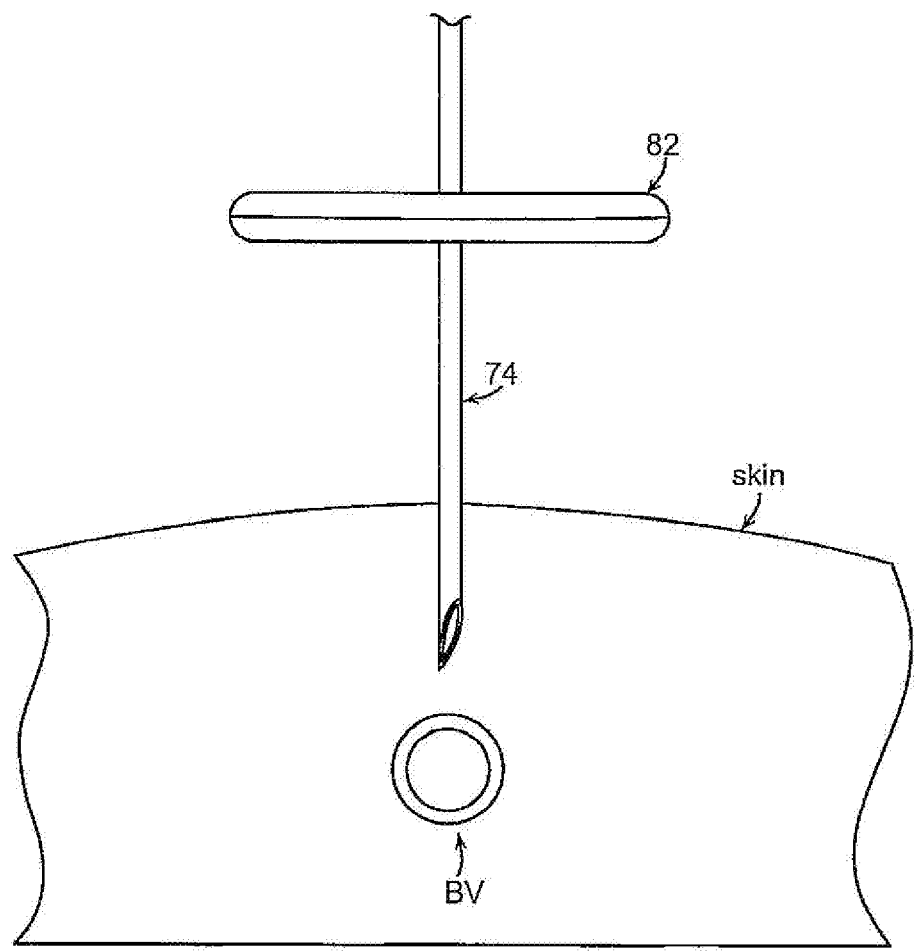
Figure 31:
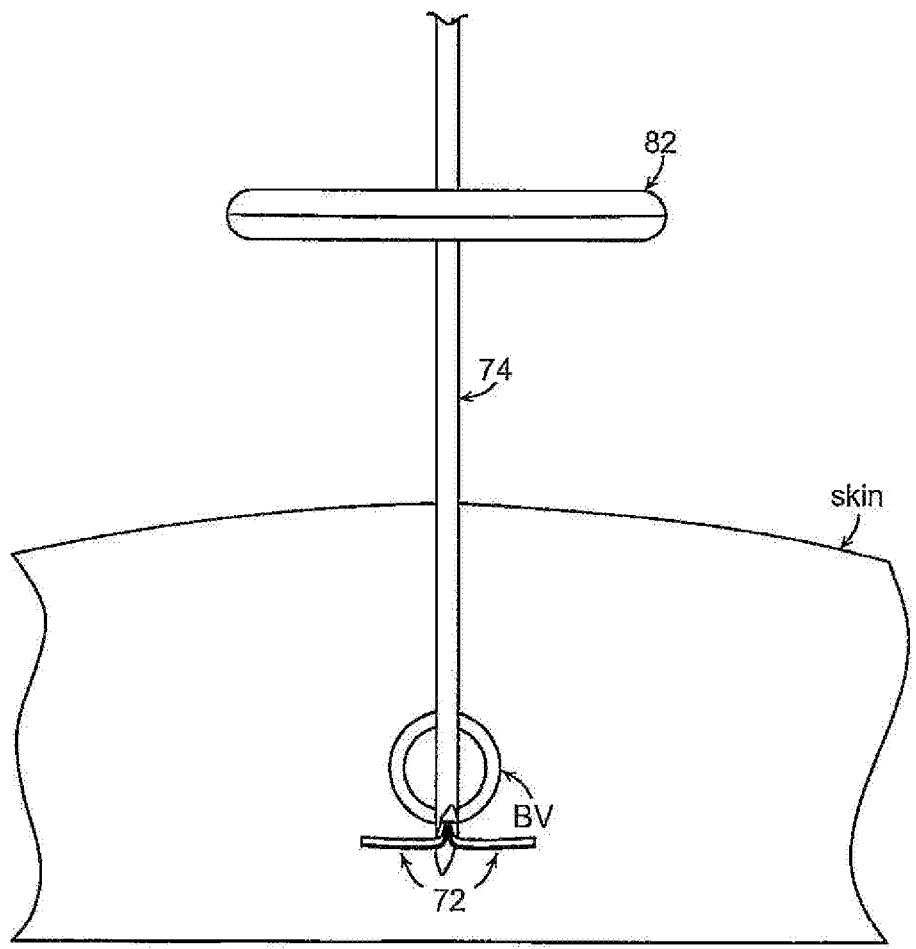
Figure 32:
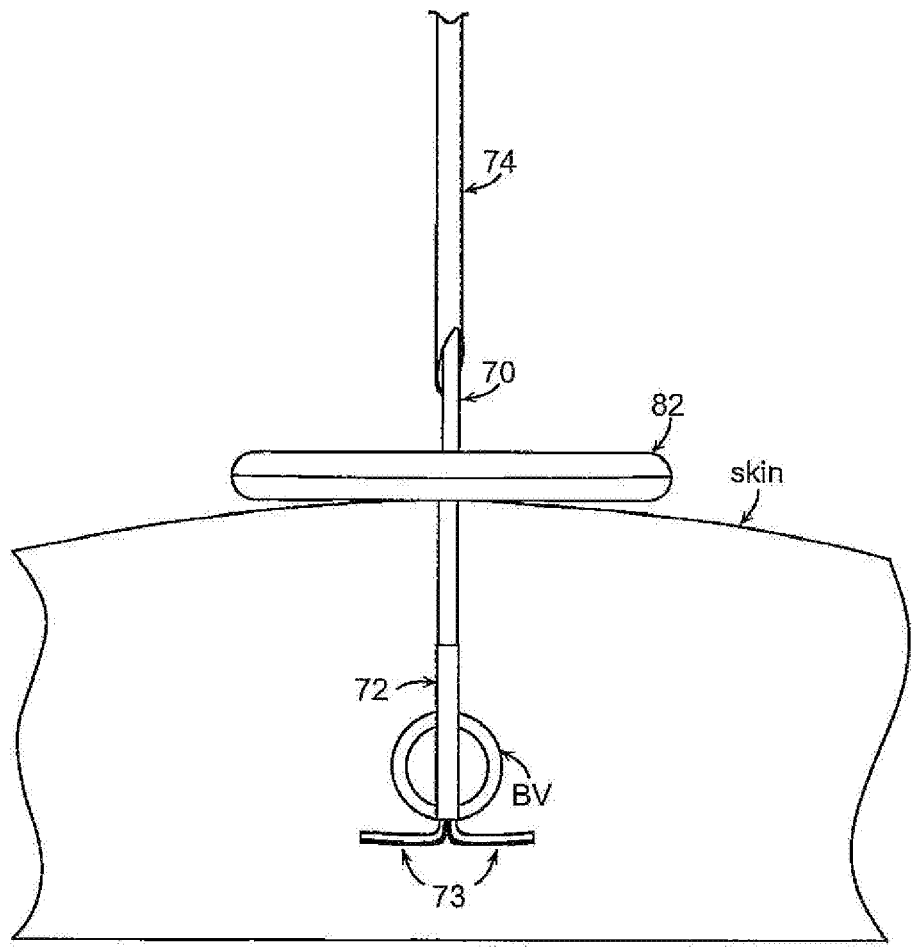
Figure 33:
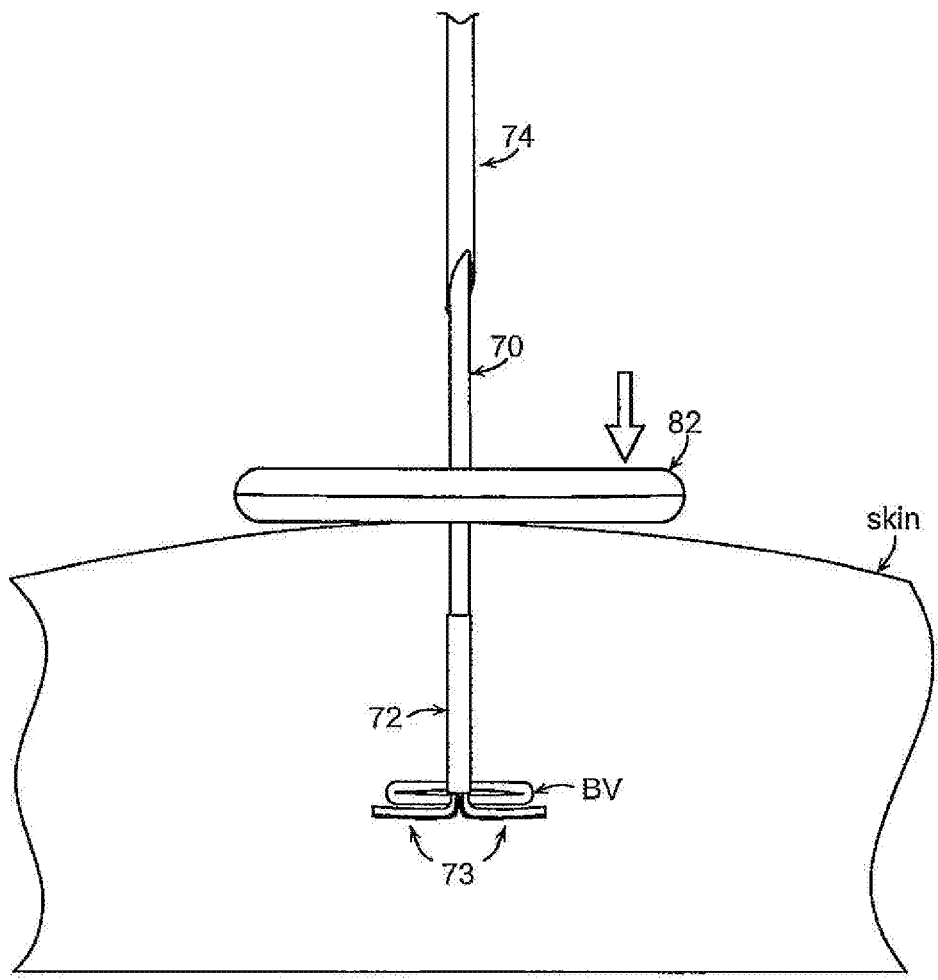
Figure 36:
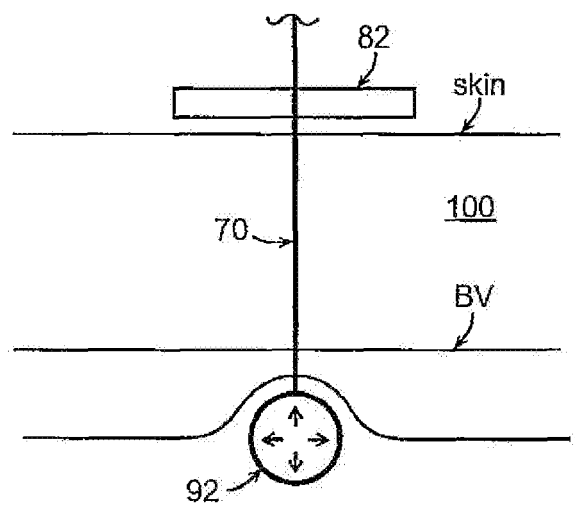
FIG. 36 illustrates, diagrammatically, a variation of the balloon embodiment of FIG. 34.

FIG. 36 illustrates another embodiment similar to that incorporates a feature of the embodiment of FIG. 28 except that the distal occluder is in the form of a balloon that is disposed on the end of an inflation line that is used to inflate and deflate the balloon. As with the embodiment of FIG. 28, the device has a proximal element 82 that is slidable on the inflation line and can be secured, adjustably, in a selected position on the line to cooperate with the balloon 92 to effect a desired degree of pressure on the blood vessel. When temporary occlusion is no longer needed, the balloon may be deflated via inflation line, and then balloon then can be pulled free of the anatomy by pulling proximally on the inflation line.

Figure 37:
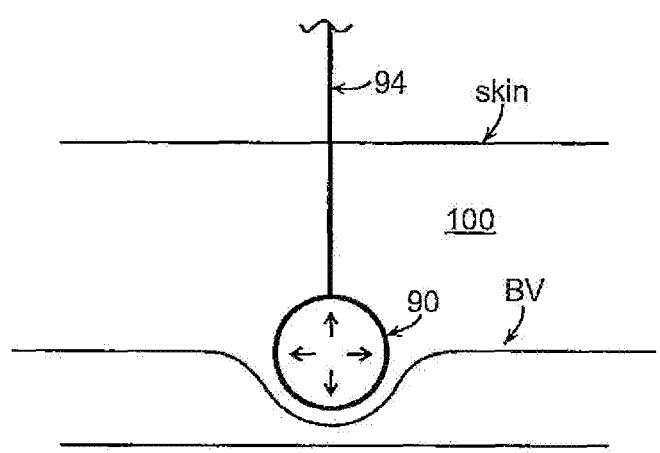
FIG. 37 illustrates a modification of the embodiment shown in FIG. 34.

FIG. 37 illustrates, diagrammatically, a further embodiment in which a single occlusion element, such as a balloon 92 or equivalent expandable element is provided on the distal end of an inflation line 70. In this embodiment the delivery needle is positioned subcutaneously with its distal end proximal of the vessel and the inflation tube is advanced through the needle to position the balloon just proximally of the vessel. The balloon then is inflated proximally of the vessel and the inflation line is urged distally to apply a compressive force to the vessel, either directly or through intervening subcutaneous tissue 100, between the balloon and tissue distal of the vessel. The force applied to the balloon can be adjusted by the EMT to adjust the degree of occlusion. When temporary occlusion is to be terminated, balloon simply is deflated via inflation line, and then balloon can be pulled free of the anatomy by pulling proximally on inflation line.

The balloons may be filled with any of a variety of gases or liquids commonly used to inflate medical balloons. In some instances, as when it is desirable to permanently maintain occlusion of the blood vessel, the balloons may be inflated with a polymer that hardens in situ.

Figure 38:
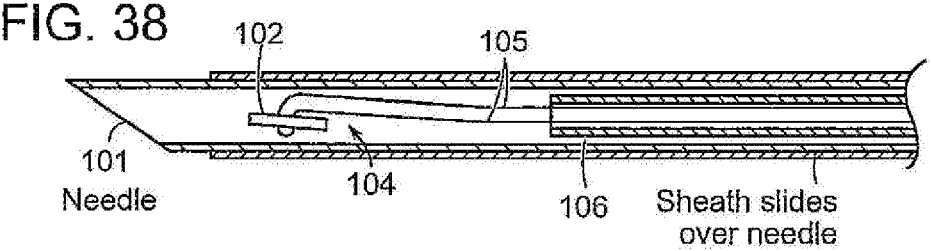
FIG. 38 is a diagrammatic illustration of another embodiment of a device for temporarily occluding a blood vessel.
Figure 39:
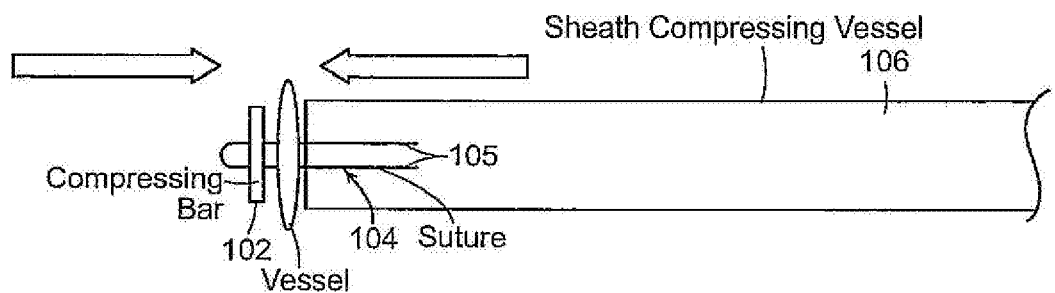
FIG. 39 is a diagrammatic illustration of the device of FIG. 38 as used to occlude a blood vessel.

FIGS. 38 and 39 illustrate, diagrammatically, another embodiment that may be employed to temporarily occlude a blood vessel. In this embodiment a needle 101 is provided and contains a compression member, such as an elongate bar 102, that is attached to a filament or suture 104. The filament is attached to the compression bar by passing it through a pair of holes formed in the compression bar with the tails 105 of the suture 104 extending through and out of the proximal end of the needle. A compression sheath 106 is slidably disposed over the needle 100. In use, the needle, loaded with the compression bar 102 and carrying the compression sheath 106, is advanced percutaneously through subcutaneous tissue to pierce the walls of the blood vessel. With the distal tip of the needle positioned distally of the vessel the compression bar is pushed out of the needle, as by a pusher element such as a tube 103 slidable within the needle. When the compression bar 102 is deployed out of the needle, tension applied to the tails of the filament 104 will cause the compression bar to reorient itself against the distal wall of the vessel (FIG. 36).

While maintaining tension on the tails of the suture to urge and maintain the bar 102 against the vessel, the compression sheath can be advanced over the needle to cause the distal end of the compression sheath to bear against the proximal wall of the vessel to compress the vessel and effect its occlusion (FIG. 36). The device may be removed by withdrawing the needle 100, filament 102 and sheath 106. The compression bar 106 may be left in place in the patient. The compression bar may be formed from a bioabsorbable material.

From the foregoing, it will be appreciated that the invention provides devices and techniques to treat, on an emergency and temporary basis, serious traumatic wounds in which significant blood loss from injured blood vessels may present a life-threatening emergency, until the injured individual can be transported to a surgical or other medical facility where the injuries can be more fully treated. It should be understood, however, that the foregoing description of the invention is intended merely to be illustrative thereof, and that other embodiments, modifications and equivalents may be apparent to those skilled in the art without departing from the principles of the invention.

We claim:

1. An apparatus for temporarily controlling blood loss from a blood vessel of a mammalian patient comprising:
   a delivery needle adapted to be advanced percutaneously through subcutaneous tissue to a location adjacent the blood vessel;
   an elongate first support member having proximal and distal ends, a distal portion of the first support member extending through the needle;
   a first occluder attached directly to the distal end of the first support member and disposed within the needle in a low-profile configuration, the first occluder being radially expandable from the low-profile configuration to a radially expanded configuration when deployed out of the needle;
   the first support member being movable through the needle to deploy the first occluder out of the needle,
   a second occluder having a low-profile configuration disposed within the delivery needle in tandem with and located distally of the first occluder, the second occluder having a radially expanded configuration when deployed out of the needle;
   an elongate, flexible tensioning member connected to the second occluder and extending proximally through the first support member and the needle;
   the tensioning member and first support member enabling the deployed occluders to be moved toward each other to effect at least partial occlusion of the blood vessel disposed between the occluders.

2. The apparatus as defined in claim 1 wherein the first support member is longitudinally flexible.

3. The apparatus as defined in claim 2 wherein the first occluder is retractable into the needle by retracting the first support member, the first occluder being configured to contract to reassume its low-profile configuration as it is retracted into the needle.

4. The apparatus as defined in claim 1 wherein the first occluder is self-expandable upon deployment from the needle.

5. The apparatus as defined in claim 1 further comprising:
   the first support member comprising a first tube;
   a second support member comprising a second tube extending slidably through the first support member, a distal end of the second support member being engageable with the second occluder to control the location and orientation of the deployed second occluder relative to the deployed first occluder.

6. The apparatus as defined in claim 5 further comprising:
   the second occluder has a tubular body and a plurality of legs that are configurable in the low profile or the radially expanded configuration;
   a pin transversely mounted to the tubular body;
   the tensioning member being engaged with the pin to enable tension applied to the tensioning member to be transmitted to the second occluder, the tensioning member extending through the second support member.

7. The apparatus as defined in claim 6 further comprising:
   a handle; the first support member and second support member being movably mounted to the handle;
   the tensioning member extending through the handle and being detachably secured to a proximal portion of the handle.

8. The apparatus as defined in claim 6 further comprising:
   each of the first and second occluders having legs that are radially expandable from the low-profile configuration to the radially expanded configuration, the legs, when both occluders are deployed, being orientable out of registry and configured to constrain the opposing walls of the blood vessel in a serpentine configuration between the deployed occluders.

9. The apparatus as defined in claim 8 further comprising:
the legs of the occluders, when deployed, being configured to interdigitate when the occluders are brought together.

10. The apparatus as defined in claim 9 wherein the legs of at least one of the occluders, when deployed, define a concave configuration.

11. The apparatus as defined in claim 10 wherein the legs of both of the occluders define concave configurations that face each other.

12. The apparatus as defined in claim 6 further comprising:
the tensioning member comprising a filament wrapped about the pin and having a pair of tails extending proximally through and out of the second support member.

13. The apparatus as defined in claim 12 further comprising:
a handle;
the first support member and second support member being movably mounted to the handle;
the tensioning member extending through the handle and being secured to a proximal portion of the handle; and
a cutting member carried by the handle and operable to sever one of the tails of the filament thereby enabling separation of the handle from the second occluder.

14. The apparatus as defined in claim 5 wherein the first and second occluders are deployable, respectively, proximally and distally of the blood vessel and wherein the deployed occluders can be drawn toward each other to apply pressure to the vessel therebetween, the degree to which the occluders compress the vessel being manually controllable by manipulation of the first support member and the tensioning member.

15. The apparatus as defined in claim 5 wherein at least one of the first and second support members comprises a tube having segments defined by transverse cuts formed on alternating sides at spaced locations along the length of the tube.

16. The apparatus as defined in claim 5 wherein each of the first support member and the second support tube comprises a tube having segments defined by transverse cuts formed on alternating sides at spaced locations along the length of the tube.

17. The apparatus as defined in claim 5 wherein the distal end of the delivery tube comprises a tissue-piercing needle.

18. The apparatus as defined in claim 1 wherein the tensioning member is detachably connected to the second occluder.

19. The apparatus as defined in claim 18 wherein the tensioning member comprises a filament and further comprising:
a cutter carried by the handle for severing the tensioning member.

20. An apparatus for controlling blood loss from a blood vessel of a mammalian patient comprising:
a handle;
a delivery tube attached to the handle and having proximal and distal ends and a lumen with an axis, the delivery tube being adapted to be advanced transversely through the walls of the blood vessel;
a proximal occluder having an axis and being disposed coaxially within the lumen of the delivery tube in a low-profile configuration, the proximal occluder being configurable to have at least a portion thereof assume a configuration oriented radially of the delivery tube axis when ejected out of the delivery tube;
a distal occluder having an axis and being disposed coaxially in a low-profile configuration within the lumen of the delivery tube distally of the proximal occluder, the proximal occluder being configurable to have at least a portion thereof assume a configuration oriented radially of the delivery tube axis when ejected out of the delivery tube;
an elongate tensioning member being detachably connected to the distal occluder and extending proximally through the delivery tube;
the distal occluder being ejectable from the delivery tube separately from and before ejection of the proximal occluder;
an elongate member extending through the delivery tube and operatively associated with the proximal occluder to urge the proximal occluder in a distal direction;
whereby, the occluders may be deployed, sequentially, on opposite sides of the vessel and may be urged toward each other to at least partially occlude the vessel in response to manipulation of the tensioning and elongate members.

* * * * *